United States Patent [19]

Hou et al.

[11] 4,241,184

[45] Dec. 23, 1980

[54] SECONDARY ALCOHOL DEHYDROGENASE ENZYME AND USE THEREOF

[75] Inventors: Ching-Tsang Hou; Ramesh N. Patel, both of Edison, N.J.; Allen I. Laskin, New York, N.Y.

[73] Assignee: Exxon Research & Engineering Co., Florham Park, N.J.

[21] Appl. No.: 24,302

[22] Filed: Mar. 27, 1979

Related U.S. Application Data

[63] Continuation-in-part of Ser. No. 896,475, Apr. 14, 1978, abandoned, and Ser. No. 896,476, Apr. 14, 1978, abandoned.

[51] Int. Cl.$^3$ .................... C12P 7/26; C12P 7/04; C12N 1/30; C12N 1/20
[52] U.S. Cl. ........................... 435/148; 435/150; 435/157; 435/160; 435/250; 435/253; 435/822; 435/858
[58] Field of Search ............... 435/148, 136, 150, 157, 435/189, 250, 253, 255, 822, 858, 938, 944, 160

[56] References Cited

U.S. PATENT DOCUMENTS

| | | | |
|---|---|---|---|
| 3,326,771 | 6/1967 | Leavitt | 435/136 X |
| 3,344,037 | 9/1967 | Leavitt | 435/136 |
| 3,930,947 | 1/1976 | Morinaga | 435/248 |

OTHER PUBLICATIONS

Colby et al., "The Soluble Methane Mono-oxygenese of *Methylococcus capsulatus*", Biochem. J., vol. 165, No. 2 (1977), pp. 395-402.
Patel et al., "Microbial Oxidation of $CH_4$ & $CH_3OH$, Crystallization & Properties of Methanol Dehydrogenase from *Methylosinus sporium*", J. Bact., vol. 128, No. 1 (1976), pp. 413-424.
Thomson et al., "Acetone Production by Methylobacteria", Chemical Abstracts, vol. 85, p. 240 (1976), Abstract No. 156225t.
Leadbetter et al., "Methane Utilizing Bacteria", Chemical Abstracts, vol. 54 (1958), Abstract No. 4747c.

*Primary Examiner*—R. B. Penland
*Attorney, Agent, or Firm*—Albert P. Halluin

[57] ABSTRACT

Disclosed is a newly-discovered and isolated enzyme which is a nicotinamide adenine dinucleotide (NAD+)-linked $C_3$-$C_6$ secondary alcohol-specific dehydrogenase. This enzyme, in the presence of oxygen and NAD, is capable of converting $C_3$-$C_6$ secondary alcohols to the corresponding methyl ketones. The purified enzyme has a molecular weight of 95,000 ± 3,000 dalton as determined by acrylamide gel electrophoresis and contains two zinc atoms per molecule of protein. Primary alcohols are not oxidized by this enzyme.

11 Claims, No Drawings

SECONDARY ALCOHOL DEHYDROGENASE ENZYME AND USE THEREOF

CROSS-REFERENCE TO RELATED APPLICATIONS

This application is a continuation-in-part of U.S. applications Ser. Nos. 896,475 and 896,476, filed Apr. 14, 1978, both now abandoned. This application is related to U.S. application Ser. No. 896,467, filed Apr. 14, 1978, now abandoned.

FIELD OF THE INVENTION

The present invention relates to newly discovered and isolated methylotrophic microorganism strains and their natural and/or artificial mutants which grow well under aerobic conditions in a culture medium in the presence of methane as the major carbon and energy source. The methane-grown microbial cells are high in protein and are useful as feedstuffs. The methane-grown microbial cells or enzyme preparations thereof are also useful in converting oxidizable substrates to oxidized products, e.g., $C_1$–$C_6$ alkanes to alcohols, $C_3$–$C_6$ alkanes to the corresponding $C_3$–$C_6$ sec. alcohols and methyl ketones, $C_3$–$C_6$ sec. alcohols to the corresponding methyl ketones, cyclic hydrocarbons to cyclic hydrocarbyl alcohols (e.g., cyclohexane to cyclohexanol), $C_2$–$C_4$ alkenes selected from the group consisting of ethylene, propylene, butene-1 and butadiene to the corresponding 1,2-epoxides, styrene to styrene oxide, etc.

BACKGROUND OF THE INVENTION

Methane is one of the most inexpensive carbon sources for microbial growth. It is known that there are many microorganisms capable of growing on a culture medium in the presence of methane as the principle carbon source. However, not all of these microorganisms share good growth characteristics. It is also known that methane-grown microorganisms can be used to convert methane to methanol under aerobic conditions.

These methane-utilizing microorganisms are generally known as "methylotrophs". The classification system for methylotrophs proposed by R. Whittenbury et al. (*J. of Gen. Microbiology*, 61, 205–218 (1970)) is the most widely recognized. In their system, the morphological characteristics of methane-oxidizing bacteria are divided into five groups: Methylosinus, Methylocystis, Methylomonas, Methylobacter and Methylococcus.

Recently, Patt, Cole and Hanson (*International J. Systematic Bacteriology*, 26, (2) 226–229 (1976)) disclosed that methylotrophic bacteria are those bacteria that can grow non-autotrophically using carbon compounds containing one or more carbon atoms but containing no carbon-carbon bonds. Patt et al. have proposed that methylotrophs should be considered "obligate" if they are capable of utilizing only carbon compounds containing no carbon-carbon bonds (e.g., methane, methanol, dimethylether, methylamines, etc.) as the sole sources of carbon and energy whereas "facultative" methylotrophs are those organisms that can use both compounds containing no carbon-carbon bonds as well as compounds having carbon-carbon bonds as the sources of carbon and energy. In their paper, Patt et al. disclosed a methane-oxidizing bacterium, which they identified as *Methylobacterium organophilum* sp nov. (ATCC 27,886). This bacterium presumably differs from all previously described genera and species of methane-oxidizing bacteria because of its ability to utilize a variety of organic substrates with carbon-carbon bonds as sources of carbon and energy.

DESCRIPTION OF THE PRIOR ART

Hutchinson, Whittenbury and Dalton (*J. Theor. Biol.*, 58, 325–335 (1976) "A Possible Role of Free Radicals in the Oxidation of Methane by *Methylococcus capsulatus*") and Colby and Dalton (*J. Biochem.*, 157, 495–497 (1976) "Some Properties of a Soluble Methane Mono-Oxygenase From *Methylococcus capsulatus* Strain Bath") reported that ethylene is oxidized by the soluble methane mono-oxygenase from *Methylococcus capsulatus* Strain Bath. The latter investigators reported that the "particulate membrane preparations" of *Methylococcus capsulatus* Strain Bath did not have methane-oxygenase activity as determined by the bromomethane disappearance test.

Cerniglia, Blevins and Perry, (*Applied and Environmental Microbiology*, 32, (6) 764–768 (1976) "Microbial Oxidation and Assimilation of Propylene") described the oxidation of propylene by microorganisms to the corresponding alcohols and carboxylic acids.

Most recently, Colby, Stirling and Dalton, (*J. Biochem.*, 165, 395–402 (August, 1977)) "The Soluble Methane Mono-Oxygenase of *Methylococcus capsulatus* (Bath) Its Ability to Oxygenate n-Alkanes, n-Alkenes, Ethers, and Alicyclic Aromatic and Heterocyclic Compounds") disclosed that the soluble fraction of *Methylococcus capsulatus* Strain Bath is a very non-specific oxygenase in that it oxidizes alkanes to alcohols, alkenes to 1,2-epoxides, dimethylether to ethanol and ethanal, styrene to styrene epoxide and pyridine to pyridine N-oxide.

On the basis of $^{18}O_2$ incorporation from $^{18}O_2$ into the cellular constituents of *Pseudomonas methanica* Leadbetter and Foster (*Nature*, 184: 1428–1429 (1959) "Incorporation of Molecular Oxygen in Bacterial Cells Utilizing Hydrocarbons For Growth") suggested that the initial oxidative attack on methane involves an oxygenase. Higgins and Quayle (*J. Biochem.*, 118: 201–208 (1970) "Oxygenation of Methane by Methane-Grown *Pseudomonas methanica* and *Methanomonas methanooxidans*") isolated $CH_3{}^{18}OH$ as the product of methane oxidation when suspensions of *Pseudomonas methanica* or *Methanomonas methanooxidans* were allowed to oxidize methane in $^{18}O_2$-enriched atmospheres. The subsequent observation of methane-stimulated NADH oxidation catalyzed by extracts of *Methylococcus capsulatus* by Ribbons (*J. Bacteriol.*, 122: 1351–1363 (1975) "Oxidation of $C_1$-Compounds by Particulate Fractions From *Methylococcus capsulatus*: Distribution and Properties of Methane-Dependent Reduced Nicotinamide Adenine Dinucleotide Oxidase (methane hydroxylase)") and Ribbons and Michalover, FEBS Lett. 11: 41–44 (1970) "Methane Oxidation by Cell-Free Extracts of *Methylococcus capsulatus*" or *Methylomonas Methanica Ferenci* (FEBS Lett. 41: 94–98 (1974) "Carbon Monoxide-Stimulated Respiration in Methane-Utilizing Bacteria") suggested that the enzyme responsible for this oxygenation is a monooxygenase. These workers relied on indirect enzyme assays, measuring methane-stimulated NADH disappearance spectrophotometrically or methane-stimulated $O_2$ disappearance polarographically. Recently, methane monooxygenase systems were partially purified from *Methylosinus trichosporium* OB3b (Tonge, Harrison and Higgins, *J. Biochem.*, 161: 333–344 (1977) "Purification and Properties of the Methane Monooxygenase Enzyme System From *Methylosinus trichosporium* OB3b"); and Tonge, Harrison, Knowles and Higgins, FEBS Lett., 58: 293-299 (1975) "Properties and Partial Purification of the Methane-Oxidizing Enzyme System From *Methylosinus trichosporium*") and *Methylococcus capsulatus* (Bath) (Colby and Dalton, *J. Biochem.*, 171: 461-468 (1978) "Resolution of the Methane Mono-Oxygenase of *Methylococcus capsulatus* (Bath) Into Three Components" and Colby, Stirling and Dalton, *J. Biochem.*, 165: 395-402 (1977) "The Soluble Methane Mono-Oxygenase of *Methylococcus capsulatus* (Bath), "Its Ability to Oxygenate n-Alkanes, n-Alkenes, Ethers, and Alicyclic, Aromatic and Heterocyclic Compounds").

The microbiological formation of methyl ketones in mammals, bacteria and fungi is well known. However, the ketone is formed by decarboxylation of a beta-keto acid and has, therefore, one less carbon atom than the precursor. On the other hand, bacterial formation of methyl ketones from n-alkanes, demonstrated first by Leadbetter and Foster (*Arch. Mikrobiol.*, 35: 92-104 (1960)) represents a unique alpha-oxidation, with no change in the carbon skeleton. However, in this letter report it was stated that the ketone formation was by co-oxidation in the presence of the growth substrate and indicated that no activity was found with the resting cells.

Phenazine methosulfate (PMS)-dependent methanol dehydrogenase has been extensively reported from many methylotrophic bacteria. This enzyme oxidizes primary alcohols from $C_1$ to $C_{10}$ but does not oxidize secondary alcohols. Nicotinamide ademine dinucleotide (NAD)-dependent alcohol dehydrogenases have been reported from liver and from yeast. These alcohol dehydrogenases oxidize primary alcohols and acetaldehyde, but have no activity on methanol. In addition, the alcohol dehydrogenases from yeast and liver also oxidize some secondary alcohols at a very low rate (<1% of their ethanol activity). NAD(P)-dependent alcohol dehydrogenases were also reported in Pseudomonas, *E. coli* and Leuconostoc. However, these enzymes were active only toward long-chain primary alcohols or hydroxy fatty acids. Recently, an NAD-linked methanol oxidizing enzyme was reported in a crude extract from yeast (Mehta, R. J., *J. Bacteriol.*, 124, 1165-1167 (1975). To our knowledge there is no report in the literature of a secondary alcohol-specific alcohol dehydrogenase (SADH) enzyme.

Since Ogata et al. (*J. Ferm. Technol.*, 48: 389-396 (1970)) first reported the assimilation of methanol by a yeast, many methanol-utilizing strains have been isolated from natural sources or found in stock culture collections. Interest in the cultivation of microorganisms on cheap and abundantly available compounds, such as methanol has increased greatly as a result of the potential importance of microbial protein as a food or fodder material. The production of single-cell protein (SCP) from methanol-grown yeasts have been discussed in several publications. Oxidation of methanol and other primary alcohols in yeasts has been shown to be catalyzed by an alcohol oxidase. Alcohol oxidase contained flavin adenine dinucleotide (FAD) as a prosthetic group. Secondary alcohols were not oxidized by this alcohol oxidase.

BRIEF DESCRIPTION OF THE PRESENT INVENTION

It has now been discovered that certain newly discovered and isolated methylotrophic microorganism strains and their natural and/or artificial mutants thereof grow well under aerobic conditions in a culture medium in the presence of methane as the major carbon and energy source. The methane-grown microbial cells possess a high content of protein and can be utilized as such as feedstuffs. The methane-grown microbial cells or enzyme preparations thereof are also useful in converting oxidizable substrates to oxidation products, e.g., $C_1$-$C_6$ alkanes to alcohols, particularly methane to methanol, $C_3$-$C_6$ alkanes to the corresponding secondary alcohols and methyl ketones, $C_3$-$C_6$ sec. alcohols to the corresponding methyl ketones, cyclic hydrocarbons to cyclic hydrocarbyl alcohols (e.g., cyclohexane to cyclohexanol), $C_2$-$C_4$ alkenes selected from the group consisting of ethylene, propylene, butene-1, and butadiene to 1,2-epoxides, styrene to styrene oxide, etc.

It has also been discovered that these newly discovered and isolated methylotrophic microorganism strains, including new yeast strains, may be aerobically grown on a plurality of methyl radical donating carbon-containing compounds, such as methanol, methylamine, methyl formate, methyl carbonate, dimethyl ether, etc., to produce microbial cells or enzyme preparations capable of aerobically converting $C_3$-$C_6$ linear secondary alcohols to the corresponding methyl ketones.

As an additional discovery we have identified a nicotinamide adenine dinucleotide (NAD)-dependent secondary alcohol dehydrogenase in cell-free extracts of various hydrocarbon-utilizing microbes, including bacteria and yeast. This enzyme is also found in cells grown on methanol. It specifically and stoichiometrically oxidizes $C_3$-$C_6$ secondary alcohols to their corresponding methyl ketones. This enzyme has been purified 2600 fold and shows a single protein band on acrylamide gel electrophoresis. It has a molecular weight of 95,000 dalton. The bacterial SADH consists of two subunits of 48,000 dalton and to atoms of zinc per molecule of enzyme protein. It oxidizes secondary alcohols, notably 2-propanol and 2-butanol. Primary alcohols are not oxidized by SADH.

DETAILED DESCRIPTION OF THE PRESENT INVENTION

The term "microorganism" is used herein in its broadest sense to include not only bacteria, but also yeasts, filamentous fungi, actinomycetes and protozoa. Preferably, the microorganisms will include bacteria, and more preferably the bacteria capable of oxidizing methane and methyl-radical donating carbon-containing compounds.

The term "enzyme preparation" is used to refer to any composition of matter that exhibits the desired oxygenase or dehydrogenase enzymatic activity. The term is used to refer, for example, to live whole cells, dried cells, cell extracts and refined and concentrated preparations derived from the cells, especially purified secondary alcohol dehydrogenase and its NAD+ cofactor and metal requirement. Enzyme preparations may be either in dry or liquid form. The term also includes the immobilized form of the enzyme, e.g., the whole cells of the methane or methyl-radical-grown microorganisms or enzyme extracts immobilized or bound to an insoluble matrix by covalent chemical linkages, absorption and entrapment of the enzyme within a gel lattice having pores large enough to allow the molecules of the substrate and of the product to pass freely, but small enough to retain the enzyme. The term "enzyme preparation" also includes enzymes retained within hollow fiber membranes, e.g., as disclosed by Rony, *Biotechnology and Bioengineering* (1971).

The term "particulate fraction" refers to the enzyme activity in the precipitated or sedimented material when the supernatant after centrifuging broken cells at $10,000 \times g$. for 30 minutes is centrifuged for 1 hour at $10,000 \times g$. or greater.

The term "increasing the oxidative state of an oxidizable organic substrate" is meant to include incorporating oxygen in an organic compound, such as in epoxidizing olefins and converting alkanes to alcohols or ketones or increasing the oxidative state of oxygen-containing compounds such as converting alcohols to aldehydes and ketones (i.e., a dehydrogenating reaction). Specifically preferred processes where the methane or methyl-radical-grown microbial cells or their enzyme preparations are used to increase the oxidative state of an oxidizable organic substrate include: converting $C_2$–$C_4$ alkenes selected from the group consisting of ethylene, propylene, butene-1 and butadiene to 1,2-epoxides; converting $C_1$–$C_6$ alkanes to corresponding alkanols; converting $C_3$–$C_6$ sec. alcohols to the corresponding methyl ketones. In this regard, microbial cells or enzyme preparations of methane-grown *Methylobacter vinelandii* M5Y NRRL B-11,218 and mutants thereof converts cyclohexane to cyclohexanol.

The classification system of methane-oxidizing bacteria proposed by R. Whittenbury, K. C. Phillips and J. F. Wilkinson [*J. Gen. Microbiology*, 61, 205–218 (1970) (hereinafter Whittenbury et al.)] is the most widely recognized system used today. In this system of classification, based on morphological characteristics methane-utilizing bacteria are divided into five groups. They are: Methylosinus, Methylocystis, Methylomonas, Methylobacter and Methylococcus. Bacteria of these five groups reported by Whittenbury et al. utilize methane, dimethyl ether, and methanol for growth energy and they were all reported as strictly aerobic and gram-negative.

As one embodiment of the present invention, we have discovered and isolated several new strains which grow well on a culture medium in the presence of oxygen and methane and methyl-radical donating compounds such as methanol, methylamine, methyl formate, methyl carbonate, dimethyl ether, etc. These newly discovered and isolated strains of methylotrophic microorganisms are capable of producing microbial cells useful as feedstuffs when cultured under aerobic conditions in a liquid growth medium comprising assimilable sources of nitrogen and essential mineral salts in the presence of methane gas or the above-mentioned methyl-radical donating carbon-containing compounds as the major carbon and energy source.

As another embodiment of the invention there is provided biologically pure isolates and mutants thereof of a plurality of newly discovered and isolated methane-utilizing microorganism strains. These biologically pure isolates (described in more detail below) are capable of producing microbial cells when cultivated in an aerobic nutrient medium containing methane or the above-mentioned methyl-radical donating carbon-containing compounds as the major carbon and energy source.

As still another embodiment of the invention there is provided a process for increasing the oxidative state of an oxidizable organic substrate which comprises contacting, under aerobic conditions, in a medium comprising assimilable sources of nitrogen and essential mineral salts, microbial cells or an enzyme preparation thereof and an organic substrate until the oxidative state of at least a portion of said organic substrate is increased, wherein said microbial cells have been cultured, under aerobic conditions in a liquid growth medium comprising assimilable sources of nitrogen and essential mineral salts in the presence of methane gas as the major carbon and energy source wherein the microbial cells are derived from the newly discovered and isolated methane-utilizing strains of the invention (described below).

A particularly preferred embodiment of the invention includes a process for producing propylene oxide from propylene by contacting propylene under aerobic conditions with microbial cells or enzyme preparation thereof wherein the microbial cells are derived from the newly discovered and isolated methane-utilizing strains of the present invention as described below and which have been previously grown under aerobic conditions in the presence of methane.

Another particular preferred embodiment of the invention includes a process for converting $C_3$–$C_6$ linear secondary alcohols to the corresponding methyl ketones by contacting a $C_3$–$C_6$ linear secondary alcohol under aerobic conditions with microbial cells or enzyme preparations thereof (including cell extracts or purified SADH and NAD+) wherein the microbial cells are derived from the newly discovered and isolated methane or methyl-radical utilizing strains of the present invention as described below and which have been previously grown under aerobic conditions in the presence of methane or a methyl-radical donating carbon-containing compound such as methanol, methylamine, methyl formate, methyl carbonate, dimethyl ether, etc., most preferably methane or methanol.

The instant invention includes the following features:

The isolates of methane-utilizing microbes of the invention include obligate (Type I and Type II) and facultative bacteria as well as new methanol utilizing yeasts.

In addition to their ability to oxidize methane to methanol, resting cell-suspensions of several distinct types of methane-grown bacteria (e.g., Type I, obligate; Type II, obligate; and facultative)oxidize $C_2$–$C_4$ n-alkene and butadiene to their corresponding 1,2-epoxides.

The product 1,2-epoxides are not further metabolized and accumulate extracellularly.

Methanol-grown cells do not have either the epoxidation or the hydroxylation activities. Among the substrate gaseous alkenes, propylene is oxidized at the highest rate.

Methane inhibits the epoxidation of propylene.

The stoichiometry of the consumption of propylene and oxygen, and the production of propylene oxide is 1:1:1.

Results from inhibition studies indicate that the same monooxygenase system catalyzes both the hydroxylation and the epoxidation reactions.

Both the hydroxylation and epoxidation activities are located in the cell-free (enzyme extract) particulate fraction precipitated or sedimented between $10,000 \times g$. and $80,000 \times g$. centrifugation for 1 hour.

Cell-free particulate fractions from the obligate and facultative methylotroph microorganisms catalyze the hydroxylation of methane to methanol and the epoxidation of $C_2$–$C_4$ n-alkenes and dienes (e.g., ethylene, propylene, 1-butene and butadiene) in the presence of oxygen and reduced nicotinamide adenine dinucleotide (NADH) and the hydroxylation of $C_1$–$C_4$ n-alkanes (e.g., methane, ethane, propane and butane).

The hydroxylation and epoxidation activities of the methane-grown methylotrophs are lost simultaneously during storage and are strongly inhibited by various metal-binding agents.

The stoichiometry for the consumption of substrate (propylene or methane), oxygen, NADH, and product formation was found to be approximately 1:1:1:1.

Resting-cell suspensions of the new $C_1$-utilizing microbes oxidize (dehydrogenate) $C_3$–$C_6$ secondary alcohols to their corresponding methyl ketones. The product methyl ketones accumulate extracellularly. Among the secondary alcohols, 2-butanol was oxidized at the highest rate.

Succinate-grown cells of the new facultative methylotrophs isolates do not convert secondary alcohols to methyl ketones.

Some enzymatic degradation of 2-butanone was observed. The product, 2-butanone, did not inhibit the conversion of 2-butanol to the corresponding 2-butanone. The rate of the 2-butanone production was linear for the first four hours of incubation for the cultures tested.

A yeast culture had the highest production rate and had a higher temperature optimum (40° C.) and there was a reasonably high 2-butanone production rate at 45° C. (The bacteria had a temperature optimum of about 35° C.)

Metal-chelating agents inhibit the production of 2-butanone which suggests the involvement of metal(s).

Secondary alcohol dehydrogenase activity was found in the cell-free soluble extract of the sonically disrupted cells of the $C_1$-grown isolates. The cell-free system requires a cofactor, specifically NAD, for its activity. The new secondary alcohol dehydrogenase specifically and stoichiometrically oxidizes $C_3$–$C_6$ secondary alcohols to their corresponding methyl ketones. The enzyme has been purified 2,600 fold and shows a single protein band on acrylamide gel electrophoresis. It has a molecular weight of 95,000 dalton. The bacterial SADH consists of two subunits of 48,000 dalton and two atoms of zinc per molecule of enzyme protein. Primary alcohls are not converted to ketones by the SADH. The pH and temperature optima for SADH are 8–9, and 30°–35° C., respectively. The activation energy calculated is 19.8 K cal. Acrylamide gel electrophoresis of the purified SADH fraction stained with coomassie brilliant blue and activity stain, as well as the crude soluble cell-free extracts from distinct types of methanol-grown microbes stained with activity stain were compared. Both the protein stain and the enzyme activity stain of the purified SADH showed a single protein band. The mobility on the gel electrophoresis of SADH from the distinct types of methanol-grown bacterial cells were identical. Yeast SADH had faster mobility toward anode on the gel electrophoresis. The addition of substrates in the SADH reaction does not require an obligatory order. The SADH activity is inhibited by metal-chelating agents, by strong thio-reagents, and by the product 2-butanone.

Cell suspensions of yeasts of the invention grown on methyl radical donating compounds (e.g., methanol, methylamine, methyl formate, etc.) catalyze the conversion of secondary alcohols to the corresponding methyl ketones.

Cell-free extracts derived from methyl-raadical (e.g., methanol)-grown yeasts of the invention catalyzed an $NAD^+$-dependent oxidation of $C_3$–$C_6$ secondary alcohols to the corresponding methyl ketones. The purified $NAD^+$-specific secondary alcohol dehydrogenase from methanol-grown yeast of the invention is homogeneous as judged by polyacrylamide gel electrophoresis. The purified enzyme catalyzes the conversion of secondary alcohols to the corresponding methyl ketones in the presence of $NAD^+$ as an electron acceptor. Primary alcohols were not oxidized by the purified enzyme. The optimum pH for conversion of secondary alcohols by the purified yeast-derived enzyme is 8. The molecular weight of the purified yeast-derived SADH as determined by gel filtration is 98,000 and subunit size as determined by sodium dodecyl sulfate gel electrophoresis is 48,000. The activity of the purified yeast-derived SADH was inhibited by sulfhydryl inhibitors and metal-binding agents.

$C_3$–$C_6$ n-alkanes are converted to $C_3$–$C_6$ sec. alcohols by cell suspensions of the methane-grown methylotrophs of of the invention and the secondary alcohols accumulate extracellularly. Other microorganisms, e.g., yeasts, actinomycetes, and fungi, grown on $C_1$-compounds will oxidize the $C_3$–$C_6$ n-alkanes to the corresponding sec. alcohols.

$C_3$–$C_6$ n-alkanes are converted to $C_3$–$C_6$ sec. alcohols by cell-free particulate fractions derived from the methylotrophic microorganisms of the invention. The reaction requires oxygen and reduced nicotinamide adenine dinucleotide (NADH) as electron donor. The conversion of the n-alkanes to the sec. alcohols is inhibited by thio-containing compounds and metal-binding agents such as $\alpha,\alpha$-bipyridyl, thiosemicarbazide, thiourea, 1,10-phenanthroline, and 8-hydroxyquinoline. (This suggests the involvement of metal ion(s) in the oxidation of $C_3$–$C_6$ n-alkanes to sec. alcohols.) The hydroxylation of $C_3$–$C_6$ n-alkanes to the corresponding sec. alcohols is inhibited in the presence of propylene. This suggests that the propylene and n-alkanes (e.g., propane) are competing for the same enzyme system(s). Ascorbate and reduced nicotinamide adenine dinucleotide phosphate (NADPH) could also be utilized as electron donor in place of NADH for hydroxylation of n-alkanes to the corresponding sec. alcohols.

The newly discovered and isolated methane and methyl-radical-utilizing (methylotrophic) microorganism strains of the present invention have the following identifying characteristics:

TABLE I

| | Methylotropic Microorganism Strain Name | ER & E Designation | U.S.D.A. Agriculture Research Center Designation |
|---|---|---|---|
| 1. | Methylosinus trichosporium | (CRL 15 PM1) | NRRL B-11,202 |
| 2. | Methylosinus sporium | (CRL 16 PM2) | NRRL B-11,203 |
| 3. | Methylocystis parvus | (CRL 18 PM4) | NRRL B-11,204 |
| 4. | Methylomonas methanica | (CRL M4P) | NRRL B-11,205 |
| 5. | Methylomonas methanica | (CRL 21 PM7) | NRRL B-11,206 |

TABLE I-continued

| | Methylotropic Microorganism Strain Name | ER & E Designation | U.S.D.A. Agriculture Research Center Designation |
|---|---|---|---|
| 6. | *Methylomonas albus* | (CRL M8Y) | NRRL B-11,207 |
| 7. | *Methylomonas streptobacterium* | (CRL 17 PM3) | NRRL B-11,208 |
| 8. | *Methylomonas agile* | (CRL 22 PM9) | NRRL B-11,209 |
| 9. | *Methylomonas rubrum* | (CRL M6P) | NRRL B-11,210 |
| 10. | *Methylomonas rubrum* | (CRL 20 PM6) | NRRL B-11,211 |
| 11. | *Methylomonas rosaceus* | (CRL M10P) | NRRL B-11,212 |
| 12. | *Methylomonas rosaceus* | (CRL M7P) | NRRL B-11,213 |
| 13. | *Methylobacter chroococcum* | (CRL M6) | NRRL B-11,214 |
| 14. | *Methylobacter chroococcum* | (CRL 23 PM8) | NRRL B-11,215 |
| 15. | *Methylobacter bovis* | (CRL M1Y) | NRRL B-11,216 |
| 16. | *Methylobacter bovis* | (CRL 19 PM5) | NRRL B-11,217 |
| 17. | *Methylobacter vinelandii* | (CRL M5Y) | NRRL B-11,218 |
| 18. | *Methylococcus capsulatus* | (CRL M1) | NRRL B-11,219 |
| 19. | *Methylococcus minimus* | (CRL 24 PM12) | NRRL B-11,220 |
| 20. | *Methylococcus capsulatus* | (CRL 25 PM13) | NRRL B-11,221 |
| 21. | *Methylobacterium organophilum* | (CRL 26 R6) | NRRL B-11,222 |
| 22. | Pichia sp. | (CRL-72) | NRRL Y-11,328 |
| 23. | Torulopsis sp. | ($A_1$) | NRRL Y-11,419 |
| 24. | Kloeckera sp. and mutants therof. | ($A_2$) | NRRL Y-11,420 |

An important characteristic of the strains of the present invention (as identified above) is their capability to produce microbial cells when cultured under aerobic conditions in a liquid growth medium comprising assimilable sources of nitrogen and essential mineral salts in the presence of methane gas or a methylradical donating carbon-containing compounds such as methanol, methylamine, methyl formate, methyl carbonate, dimethyl ether, etc. as the major carbon and energy source.

The above strains have been deposited at the United States Department of Agriculture, Agriculture Research Service, Northern Regional Research Laboratory (NRRL), Peoria, Ill. 61604 and have received from NRRL the individual NRRL designations as indicated above pursuant to a contract between NRRL and the assigned of this patent application (Exxon Research and Engineering Company (ER&E)). The contract with NRRL provides for permanent availability of the progeny of these strains to the public including citizens of West Germany, upon the issuance of the U.S. patent or the publication of a German patent application corresponding to this application, whichever comes first occurs and that progemy of these strains will be made available to one determined by the U.S. Commissioner of Patents and Trademarks to be entitled thereto accoding to 35 USC 122 and the Commissioner's rules pertaining thereto (including 35 CRF 1.14, with particular reference to 886 OG 638) or the West German Patent Office. The assignee of the present application had agreed that, if any of these strains on deposit should die, or is destroyed, during the effective life of the patent, it will be replaced with a living strain of the same organism.

The Taxonomical characteristics of these newly isolated strains are shown below:

MORPHOLOGICAL AND TAXONOMICAL CHARACTERISTICS OF METHYLOTROPHIC MICROORGANISMS

1. *Methylosinus trichosporium* strain CRL 15 PM1 (NRRL B-11,202) produces white round colonies on salt agar plates in the presence of $CH_4$ or $CH_3OH$. The organisms are motile, rod-shaped, gram-negative, aerobic. Rosettes frequently formed in old culture. Organisms form exospores. Grows at the expense of methane and methanol. Organic compounds other than $C_1$ compounds do not support growth. It has a Type I membrane structure.

2. *Methylosinus sporium* strain CRL 16 PM2 (NRRL B-11,203) Produces white colonies on salt agar plates in the presence of $CH_4$ or $CH_3OH$. The organisms are motile, vibrio-shaped, gram-negative, aerobic. Rosettes frequently formed. Organisms form exospores. Grows at the expense of methane and methanol. Organic compounds other than $C_1$ compounds do not support growth. It has a Type II membrane structure.

3. *Methylocystis parvus* strain CRL 18 PM4 (NRRL B-11,204) Produces mucoid white colonies on salt agar plates in the presence of $CH_4$ or $CH_3OH$. The organisms are non-motile, cocco-bacillus shaped, gram-negative, aerobic. Old cultures form cysts which are dessication-resistant. Grows at the expense of methane and methanol. Organic compounds other than $C_1$ compounds do not support growth. It has a Type II membrane structure.

4. *Methylomonas methanica* CRL M4P (NRRL B-11,205) Produces pink raised colonies on salt agar plates in the presence of $CH_4$ or $CH_3OH$. The organisms are motile, rod-shaped, gram-negative, aerobic. Produces slimy capsule. It has a Type I membrane structure.

5. *Methylomonas methanica* CRL 21 PM7 (NRRL B-11,206) Produces pink colonies on salt agar plates in the presence of $CH_4$ or $CH_3OH$. The organisms are motile, rod-shaped, gram-negative, aerobic. Produces slimy capsule. Grows at the expense of methane and methanol. Organic compounds other than $C_1$ compounds do not support growth. It has a Type I membrane structure.

6. *Methylomonas albus* CRL M8Y (NRRL B-11,207) Produces white to yellow (with age) and fuzzy-edged colonies on salt agar plates in the presence of $CH_4$ or $CH_3OH$. The organisms are rod-shaped, motile, gram-negative, aerobic. Produces slimy capsule. It has a Type I membrane structure.

7. *Methylomonas streptobacterium* CRL 17 PM3 (NRRL B-11,208) Produces white colonies on salt agar plates in the presence of $CH_4$ or $CH_3OH$. The organisms are non-motile, rod-shaped, gram-negative, aerobic. Produces slimy capsule. Grows at the expense of methane and methanol. Organic compounds other than $C_1$ compounds do not support growth. It has a Type I membrane structure.

8. *Methylomonas agile* CRL 22 PM9 (NRRL B-11,209) Produces white colonies on salt agar plates in the presence of $CH_4$ or $CH_3OH$. The organisms are non-motile, rod-shaped, gram-negative, aerobic. Grows at the expense of methane and methanol. Organic compounds other than $C_1$ compounds do not support growth. It has a Type I membrane structure.

9. *Methylomonas rubrum* CRL M6P (NRRL B-11,210) Produces pink-orange, circular and raised colonies on salt agar plates in the presence of $CH_4$ or $CH_3OH$. The organisms are rod-shaped, motile, gram-negative, aerobic. Produces slimy capsule. It has a Type I membrane structure.

10. *Methylomonas rubrum* CRL 20 PM6 (NRRL B-11,211) Produces red colonies on salt agar plates in the presence of $CH_4$ or $CH_3OH$. The organisms are motile, rod-shaped, gram-negative, aerobic. Produces slimy capsule. Grows at the expense of methane and methanol. Organic compounds other than $C_1$ compounds do not support growth. It has a Type I membrane structure.

11. *Methylomonas rosaceus* CRL M10P (NRRL B-11,212) Produces pink and circular colonies on salt agar plates in the presence of $Ch_4$ or $CH_3OH$. The organisms are motile, long thin rods, gram-negative, aerobic. It has a Type I membrane structure.

12. *Methylomonas rosaceus* CRL M7P (NRRL B-11,213) Produces pink and fuzzy-edged colonies on salt agar plates in the presence of $CH_4$ or $CH_3OH$. The organisms are small thin rods, motile, gram-negative, aerobic. Produces slimy capsule. It has a Type I membrane structure.

13. *Methylobacter chroococcum* CRL M6 (NRRL B-11,214) Produces cream-colored and fuzzy-edged colonies on salt agar plates in the presence of $CH_4$ or $CH_3OH$. The organisms are non-motile, large rlds/cocci, gram-negative, aerobic. Produces slimy capsule. It has a Type I membrane structure.

14. *Methylobacter chroococcum* CRL 23 PM8 (NRRL B-11,215) Produces pale pink colonies on salt agar plates in the presence of $CH_4$ or $Ch_3OH$. The organisms are non-motile, gram-negative, aerobic. Produces slimy capsule. Grows at the expense of methane and methanol. Organic compounds other than $C_1$ compounds do not support growth. It has a Type I membrane structure.

15. *Methylobacter bovis* CRL M1Y (NRRL B-11,216) Produces yellow, circular colonies on salt agar plates in the presence of $CH_4$ or $CH_3OH$. The organisms are non-motile large rods, gram-negative, aerobic. It has a Type I membrane structure.

16. *Methylobacter bovis* CRL 19 PM 5 (NRRL B-11,217) Produces white to brown colonies on salt agar plates in the presence of $CH_4$ or $CH_3OH$. The organisms are non-motile, gram-negative, aerobic. Produces slimy capsule. Grows at the expense of methane and methanol. Organic compounds other than $C_1$ compounds do not support growth. It has a Type I membrane structure.

17. *Methylobacter vinelandii* CRL M5Y (NRRL B-11,218) Produces small distinct, light colored (to yellow with age)—colonies on salt agar plates in the presence of $CH_4$ or $CH_3OH$. The organisms are motile, rod-shaped gram-negative, aerobic. It has a Type I membrane structure.

18. *Methylococcus capsulatus* CRL M1 (NRRL b-11,219) Produces white colonies on salt agar plates in the presence of $CH_4$ or $CH_3OH$. The organisms are non-motile, cocci, gram-negative, aerobic. It has a Type I membrane structure.

19. *Methylococcus minimus* CRL 24 PM12 (NRRL B-11,220) Produces white colonies on salt agar plates in the presence of $CH_4$ or $CH_3OH$. The organisms are non-motile cocci, gram-negative, aerobic. Sometimes organisms occur in chains and have the ability to grow at 37° and 45° C. Grows at the expense of methane and methanol. Organic compounds other than $C_1$ compounds do not support growth. It has a Type I membrane structure.

20. *Methylococcus capsulatus* CRL 25 PM13 (NRRL B-11,221) Produces white colonies on salt agar plates in the presence of $CH_4$ or $CH_3OH$. The organisms are non-motile cocci, occurs in pairs, gram-negative, aerobic. Organisms form capsules and have the ability to grow at 37° and 45° C. Grows at the expense of methane and methanol. Organic compounds other than $C_1$ compounds do not support growth. It has a Type I membrane structure.

21. *Methylobacterium organophilum* CRL 26 R6 (NRRL B-11,222) Produces white colonies on salt agar plates in the presence of methane or methanol. The organisms are motile, rod-shaped, gram-negative, aerobic. Grows at the expense of methane, methanol, glucose, succinate and nutrient agar. (Therefore, it is classically a facultative type). It has a Type I membrane structure.

22. *Pichia* sp. CRL-72 (NRRL Y-11,328) Produces slimy white colonies on plates. Cells are large and oval; some cells have buds. Reproduce by budding and they grow aerobically on $C_1$–$C_6$ primary alcohols, $C_1$–$C_4$ primary amines, methyl formate, succinate and nutrient agar. They do not grow on methane.

23. *Torulopsis* sp. $A_1$ (NRRL Y-11,419) Capable of growth on methanol, methyl formate, methylamine, ethanol, propylamine, and nutrient agar. Does not grow on methane. Cells are large oval shape and show multilateral budding under microscopic examination.

24. *Kloeckera* sp. $A_2$ (NRRL Y-11,420) Capable of growth on methanol, methyl formate, methylamine, ethanol, propylamine, and nutrient agar. Does not grow on methane. Cells are large oval shape and show bipolar budding under microscopic examination.

The newly discovered and isolated strains of the present invention were obtained from soil samples from the Bayway Refinery in Linden, N.J., and from lake water samples from Warinaco Park, Linden, N.J., and from Robert's Pond, Ridgefield, Conn. The samples were screened for methylotrophic microorganisms by growth under oxygen and methane. The methylotrophs were then isolated, purified, and maintained by the procedure described below.

The maintenance of the cultures of these newly discovered and isolated strains should be carefully controlled. The preferred means for maintaining the cultures is described below in Table II.

TABLE II

MAINTENANCE OF CULTURES

The organisms are perferably subcultured every two weeks on mineral salts agar plates which contain medium having the following composition:

| | |
|---|---|
| $Na_2HPO_4$ | 0.21 g |
| $NaH_2PO_4$ | 0.09 g |
| $NaNO_3$ | 2.0 g |
| $MgSO_4 \cdot 7H_2O$ | 0.2 g |
| KCl | 0.04 g |
| $CaCl_2$ | 0.015 g |
| $FeSO_4 \cdot 7H_2O$ | 1 mg |
| $CuSO_4 \cdot 5H_2O$ | 0.01 mg |
| $H_3BO_4$ | 0.02 mg |
| $MnSO_4 \cdot 5H_2O$ | 0.14 mg |
| $ZnSO_4$ | 0.02 mg |
| $MoO_3$ | 0.02 mg |
| Agar | 15 g |

TABLE II-continued

MAINTENANCE OF CULTURES

The organisms are preferably subcultured every two weeks on mineral salts agar plates which contain medium having the following composition:

| | |
|---|---|
| Water | 1 liter |

In the case of yeast cells, yeast nitrogen base is added to the above medium.

These plates should be incubated in glass dessicators which have lids with an airtight seal and external sleeves with a tooled hose connection. Dessicators are to be evacuated and filled with a gas mixture of methane and air (1:1 v/v). Incubation should be at 30° C. Cultures will survive in these dessicators for three months at 4° C. However, frequent transfer of cultures is preferred.

In commercial processes for the propagation of microorganisms, it is generally necessary to proceed by stages. These stages may be few or many, depending on the nature of the process and the characteristics of the microorganisms. Ordinarily, propagation is started by inoculating cells from a slant of a culture into a presterilized nutrient medium usually contained in a flask. In the flask, growth of the microorganisms is encouraged by various means, e.g., shaking for thorough aeration, and maintenance of suitable temperature. This step or stage is repeated one or more times in flasks or vessels containing the same or larger volumes of nutrient medium. These stages may be conveniently referred to as culture development stages. The microorganisms with or without accompanying culture medium, from the last development stage, are introduced or inoculated into a large scale fermentor to produce commercial quantities of the microorganisms or enzymes therefrom.

Reasons for growing the microorganisms in stages are manyfold, but are primary dependent upon the conditions necessary for the growth of the microorganisms and/or the production of enzymes therefrom. These include stability of the microorganisms, proper nutrients, pH, osmotic relationships, degree of aeration, temperature and the maintenance of pure culture conditions during fermentation. For instance, to obtain maximum yields of the microbial cells, the conditions of fermentation in the final stage may have to be changed somewhat from those practiced to obtain growth of the microorganisms in the culture development stages. Maintaining the purity of the medium, also, is an extremely important consideration, especially where the fermentation is performed under aerobic conditions as in the case of the methylotroph microorganisms. If the fermentation is initially started in a large fermentor, a relatively long period of time will be needed to achieve an appreciable yield of microorganisms and/or oxidative and dehydrogenase enzymes therefrom. This, of course, enhances the possibility of contamination of the medium and mutation of the microorganisms.

The culture media used for growing the methylotrophic microorganisms and inducing the oxidative enzyme system will be comprised of inorganic salts of phosphate, sulfates and nitrates as well as oxygen and a source of $C_1$ compounds. The fermentation will generally be conducted at temperatures ranging from 5° to about 50° C., preferably at temperatures ranging from about 25° C. to about 45° C. The pH of the culture medium should be controlled at a pH ranging from about 4 to 9 and preferably from about 5.5 to 8.5 and more preferably from 6.0 to 7.5. The fermentation may be conducted at atmospheric pressures although higher pressures up to about 5 atmospheres and higher may be employed.

Typically, to grow the methylotrophic microorganisms and to induce the oxygenase and dehydrogenate enzymes, the microorganisms are inoculated into the medium which is contacted with a gas mixture containing methane and oxygen. Methane may be supplied in the form of natural gas. For continuous flow culture the microorganisms may be grown in any suitably adapted fermentation vessel, for example, a stirred baffled fermentor or sparged tower fermentor, which is provided either with internal cooling or an external recycle cooling loop. Fresh medium may be continuously pumped into the culture at rated equivalent to 0.02 to 1 culture volume per hour and the culture may be removed at a rate such that the volume of culture remains constant. A gas mixture containing methane and oxygen and possibly carbon dioxide or other gases is contacted with the medium preferably by bubbling continuously through a sparger at the base of the vessel. The source of oxygen for the culture may be air, oxygen or oxygen-enriched air. Spent gas may be removed from the head of the vessel. The spent gas may be recycled either through an external loop or internally by means of a gas inducer impeller. The gas flows and recycle should be arranged to give maximum growth of microorganism and maximum utilization of methane.

The oxygenase enzyme system may be obtained, as described above, as a crude extract, or a cell-free particulate fraction, i.e., the material which precipitates when the supernatant after centrifuging broken cells at $10,000 \times g$. for 30 min. is centrifuged for 1 hour at $10,000 \times g$. or greater. When it is desired to obtain the secondary alcohol dehydrogenase (SADH) enzyme fraction one first breaks the cells, e.g., sonication, etc., secondly removes the cellular debris, e.g., centrifuges at $10,000 \times g$. for about 20 minutes and the recovered crude SADH enzyme can thereafter be further purified by mild heat treatment, column chromatography, etc., as described in the examples below. The microbial cells may be harvested from the growth medium by any of the standard techniques commonly used, for example, flocculation, sedimentation, and/or precipitation, followed by centrifugation and/or filtration. The biomass may be dried, e.g., by freeze or spray drying and may be used in this form for further use in the oxidation reactions.

To put the invention to practice, an oxaditive or dehydrogenase enzyme preparation is obtained, such as, for example, in the manner described above, which will convert methane to methanol under oxidative conditions. It is preferred to obtain such a preparation from one of the microorganism strains (or natural and/or artificial mutant thereof) described above and grow the microorganism in a nutrient medium containing methane and oxygen as described above. The nutrient medium may be the one described by Whittenbury et al. or more preferably the culture medium described by Foster and Davis, *J. Bacteriol.*, 91, 1924–1931 (1966). In the case of yeast, a yeast nitrogen base is added.

The enzyme preparation is then brought into contact with the desired oxidizable substrate, e.g., a $C_2$–$C_4$ alkene, e.g., ethylene, propylene, butene-1 or conjugated butadiene or mixtures thereof, a cyclic compound such as cyclohexane, an alkane such as methane, ethane, propane or butane, etc., or a secondary alcohol, e.g., 2-propanol or 2-butanol in the presence of oxygen and a buffer solution or nutrient medium (e.g., the same nutrient medium used to produce the microorganism may be used except that the oxidizable substrate material has replaced the methane) and the mixture is incubated until the desired degree of conversion has been obtained. Thereafter, the oxidized roduct is recovered by conventional means, e.g., distillation, etc.

To facilitate the necessary effective contact of oxygen and the enzyme (whether it be an enzyme preparation or methylotrophic microorganisms), it is preferred, for best results, to employ a strong, finely divided air stream into a vigorously stirred dispersion of substrate in the oxidation medium that generally contains water, and a buffer which the enzyme preparation or microorganism culture is suspended. The enzyme preparation may then be separated from the liquid medium, preferably by filtration or centrifugation. The resulting oxidized product may then generally be obtained.

The process of the invention may be carried out batchwise, semi-continuously, continuously, concurrently or countercurrently. Optionally, the suspension containing the enzyme preparation or methylotrohic microorganisms and buffer solution is passed downwardly with vigorous stirring countercurrently to an air stream rising in a tube reactor. The top layer is removed from the downflowing suspension, while culture and remaining buffer solution constituents are recycled, at least partly, with more oxidative substrate and addition of fresh enzyme preparation or methylotrophic microorganisms, as required.

The growth of the methylotrophic microorganisms and the oxidation process may be conveniently coupled by conducting them simultaneously, but separately and using much higher aeration in the oxidation process (e.g., an air excess of at least twice that required for growth, preferably at least five times as much aeration). Both the growth process and the methane hydroxylation or oxidation processes may be conducted in the same reactor in sequential or simultaneous operations by alternate use of normal and strong aeration.

The invention is illustrated further by the following examples which, however, are not to be taken as limiting in any respect. All parts and percentages, unless expressly stated otherwise, are by weight.

EXAMPLE 1

A nutrient medium as described by Foster and Davis, *J. Bacteriol.*, 91, 1924–1931 (1966) having the following composition per liter was prepared:

| | |
|---|---|
| $Na_2HPO_4$ | 0.21 g. |
| $NaH_2PO_4$ | 0.09 g. |
| $NaNO_3$ | 2.0 g. |
| $MgSO_4 \cdot 7H_2O$ | 0.2 g. |
| KCl | 0.04 g. |
| $CaCl_2$ | 0.015 g. |
| $FeSO_4 \cdot 7H_2O$ | 1 mg. |
| $CuSO_4 \cdot 5H_2O$ | 0.01 mg. |
| $H_3BO_4$ | 0.02 mg. |
| $MnSO_4 \cdot 5H_2O$ | 0.02 mg. |
| $ZnSO_4$ | 0.14 mg. |
| $MoO_3$ | 0.02 mg. |

The pH of the nutrient medium was adjusted to 7.0 by the addition of acid or base and 50 ml samples of the nutrient medium was charged into a plurality of 300 ml shaker flasks. The shaker flasks were inoculated with an inoculating loop of cells from an agar plate containing homogeneous colonies of the microorganisms on the plate (the purity of the isolates was confirmed by microscopic examination). The isolates had been maintained on agar plates under an atmosphere of methane and air having a 1:1 v/v gas ratio which had been transferred every two weeks. The gaseous phase of the inoculated flasks was then replaced with a gas mixture comprised of methane and air having a ratio of 1:1 on a v/v basis. The inoculated flasks were sealed air tight and were incubated on a rotary shaker of orbital radius 2.5 cm at 250 rpm and at 30° C. for two days until turbidity in the medium had developed.

The cells were harvested by centrifugation at $10,000 \times g$. at 4° C. for 30 minutes. The cell pellet was washed twice with a 0.15 M phosphate buffer at a pH of 7.0 (containing 0.002 M $MgCl_2$). The washed cells were then suspended in a 0.15 M phosphate buffer at pH 7.0.

A 0.5 ml sample of each washed cell suspension (2 mg cells) was put into 10 ml vials at 4° C. which were sealed with a rubber cap. The gaseous phase of the vials was removed with vacuum and then was replaced with a gas mixture of the oxidative substrate (e.g., methane) and oxygen at a 1:1 v/v ratio. The vials were then incubated at 30° C. on a rotary shaker at 300 rpm. Samples of product (3 µl) were withdrawn periodically with a microsyringe and the products were analyzed by gas chromatography (ionization flame detector column).

The newly discovered and isolated microorganism strains of the present invention were each grown aerobically in the presence of methane in the manner described above. The methane-grown microbial cells were then washed, recovered and put to use in oxidizing an oxidative substrate by the procedure described above except in the case of a liquid substrate 10 µl of the substrate were used. Table III shows the results of these experiments where the oxidative substrates were methane, ethylene, propylene, butene-1 and butadiene. The methane-grown methylotrophic microorganisms did not produce any detectable epoxide product from pentene-1 or hexene-1.

TABLE III

Oxidation Conversion Rates For Methane and Lower Alkenes With Methylotrophic Microorganisms

| | Oxidative Conversion Rates (µmole/hr/mg protein)[b] | | | | |
|---|---|---|---|---|---|
| Methylotrophic Microorganism Strain Identification[a] | Methane to Methanol | Ethylene to Ethylene Oxide | Propylene to Propylene Oxide | Butene-1 to 1,2-epoxy-butane | Butadiene to 1,2-epoxy-butene |
| *Methylosinus trichosporium* (CRL 15 PM1) NRRL B-11,202 | 1.2 | 2.5 | 4.5 | 1.8 | 4.2 |
| *Methylosinus sporium* (CRL 16 PM2) NRRL B-11,203 | 1.0 | 1.3 | 3.2 | 1.2 | 2.5 |
| *Methylocystis parvus* | — | 0.9 | 1.5 | — | — |

TABLE III-continued
Oxidation Conversion Rates For Methane and Lower Alkenes With Methylotrophic Microorganisms

| Methylotrophic Microorganism Strain Identification[a] | Oxidative Conversion Rates ($\mu$mole/hr/mg protein)[b] | | | | |
|---|---|---|---|---|---|
| | Methane to Methanol | Ethylene to Ethylene Oxide | Propylene to Propylene Oxide | Butene-1 to 1,2-epoxy-butane | Butadiene to 1,2-epoxy-butene |
| (CRL 18 PM4) NRRL B-11,204 *Methylomonas methanica* | 2.3 | 1.0 | 3.8 | 2.8 | 1.0 |
| (CRL M4P) NRRL B-11,205 *Methylomonas methanica* | — | 2.1 | 2.4 | — | — |
| (CRL 21 PM7) NRRL B-11,206 *Methylomonas albus* | 1.5 | 1.8 | 2.5 | 1.8 | 3.0 |
| (CRL M8Y) NRRL B-11,207 *Methylomonas streptobacterium* | 1.1 | 0.7 | 1.0 | 2.5 | 2.6 |
| (CRL 17 PM3) NRRL B-11,208 *Methylomonas agile* | 0.6 | 2.2 | 1.6 | 0.5 | 2.0 |
| (CRL 22 PM9) NRRL B-11,209 *Methylomonas rubrum* | 0.5 | 0.7 | 1.0 | — | — |
| (CRL M6P) NRRL B-11,210 *Methylomonas rubrum* | 0.42 | 1.1 | 1.9 | — | — |
| (CRL 20 PM6) NRRL B-11,211 *Methylomonas rosaceus* | 7.3 | 4.7 | 1.41 | 3.1 | 9.2 |
| (CRL M10P) NRRL B-11,212 *Methylmonas rosaceus* | 1.4 | 2.9 | 2.0 | — | — |
| (CRL M7P) NRRL B-11,213 *Methylobacter chroococcum* | 0.8 | 1.6 | 1.2 | 0.7 | 1.5 |
| (CRL M6) NRRL B-11,214 *Methylobacter chroococcum* | 0.72 | 1.2 | 2.5 | 0.82 | 1.8 |
| (CRL 23 PM8) NRRL B-11,215 *Methylobacter bovis* | 1.5 | 0.64 | 1.5 | 1.1 | 1.27 |
| (CRL M1Y) NRRL B-11,216 *Methylobacter bovis* | 2.0 | 1.3 | 2.2 | 1.3 | 2.3 |
| (CRL 19 PM5) NRRL B-11,217 *Methylobacter vinelandii* | 0.9 | 1.2 | 1.9 | 0 | — |
| (CRL M5Y) NRRL B-11,218 *Methylococcus capsulatus* | 2.5 | 5.7 | 5.5 | 1.3 | 4.4 |
| (CRL M1) NRRL B-11,219 *Methylococcus minimus* | 2.3 | 1.2 | 1.8 | 1.5 | 3.0 |
| (CRL 24 PM12) NRRL B-11,220 *Methylococcus capsulatus* | 2.1 | 0.8 | 1.2 | 1.9 | 2.5 |
| (CRL 25 PM13) NRRL B-11,221 *Methylobacterium organophilum* | 0.7 | 0.9 | 2.5 | 0.9 | 2.8 |
| (CRL 26 R6) NRRL B-11,222 | | | | | |

[a]The dry weight of the cells was about 0.2 g/100 ml culture broth.
[b]The products of microbial oxidation were identified by gas chromatographic retention time with authentic standards. The identification of the products was supplemented by establishing the presence or absence of product peaks before and after bromination or acid hydrolysis. Analysis also revealed that no further oxidation of epoxide product occurred.

In comparative experimental tests, washed cell suspensions of the methylotrophic microorganism strains of the present invention grown on methanol did not possess the ability to either hydroxylate methane or the ability to epoxidize the $C_2$–$C_4$ alkenes.

EXAMPLE 2

The procedure of Example 1 was repeated using *Methylobacter bovis* CRL M1Y NRRL B-11,216 and *Methylococcus capsulatus* CRL M1 NRRL B-11,219 except that the microorganisms were grown in the aerobic methane nutrient medium at 40° C. The washed cells of the methane-grown cells were then contacted with propylene by the procedure described in Example 1 (30° C. reaction temperature) and the reaction product (propylene oxide) was analyzed by gas chromatography retention time. The methane-grown methylotrophic microorganisms (*Methylobacter bovis* CRL M1Y NRRL B-11,216 and *Methylococcus capsulatus* CRL M1 NRRL B-11,219 converted propylene to propylene oxide at a conversion rate of 0.27 $\mu$mole/2hr./mg. protein and 7.88 $\mu$mole/2 hr./mg. protein, respectively, wherein the dry weight of the cells was about 0.2 g./100 ml. of culture broth.

EXAMPLE 3

Microbiological Conversion of Sec. Alcohols to Ketones

The procedure in Example 1 was repeated wherein a plurality of the newly discovered and isolated strains were each grown aerobically in the methane-containing nutrient medium. The washed cells of the methane-grown methylotrophic microorganisms were then contacted with sec. alcohols, i.e., isopropanol or 2-butanol by the oxidation procedure of Example 1. The reaction products were analyzed and found to contain acetone and 2-butanone, respectively. The results of this series of experiments are shown in Table IV.

TABLE IV
Microbiological Conversion of Sec. Alcohols to Ketones

| Methylotrophic Microorganism Strain Identification | Conversion Rate to Ketone ($\mu$mole/2 mg protein) | | Product Formed (detected by GC) |
|---|---|---|---|
| | 2 hrs. | 20 hrs. | |
| Methane-Grown-Isopropanol Substrate | | | |
| 1. *Methylobactor chroococcum* (CRL M6) NRRL B-11,214 | 1 | 8 | Acetone |

TABLE IV-continued

Microbiological Conversion of Sec. Alcohols to Ketones

| Methylotrophic Microorganism Strain Identification | Conversion Rate to Ketone (μmole/2 mg protein) 2 hrs. | 20 hrs. | Product Formed (detected by GC) |
|---|---|---|---|
| 2. *Methylococcus capsulatus* (CRL M1) NRRL B-11,219 | 3 | 15 | Acetone |
| 3. *Methylosinus trichosporium* (CRL 15 PM1) NRRL B-11,202 | 3 | — | Acetone |
| 4. *Methylomonas rubrum* (CRL M6P) NRRL B-11,210 | 1 | — | Acetone |
| 5. *Methylobacter bovis* (CRL M1Y) NRRL B-11,216 | 5 | — | Acetone |
| 6. *Methylobacter organophilum* (CRL 26 R6) NRRL B-11,222 Methane-Grown-2-Butanol Substrate | 3 | — | Acetone |
| 7. *Methylosinus trichosporium* (CRL 15 PM1) NRRL B-11,202 | 20 | — | 2-Butanone |
| 8. *Methylomonas methanica* (CRL M4P) NRRL B-11,205 | 0.06 | 2 | 2-Butanone |
| 9. *Methylomonas rosaceus* (CRL M7P) NRRL B-11,213 | — | — | — |
| 10. *Methylobacter chroococcum* (CRL M6) NRRL B-11,214 | 1 | 3 | 2-Butanone |
| 11. *Methylobacter bovis* (CRL M1Y) NRRL B-11,216 | 20 | | 2-Butanone |
| 12. *Methylobacter vinelandii* (CRL M5Y) NRRL B-11,218 | 2 | 18 | 2-Butanone |
| 13. *Methylococus capsulatus* (CRL M1) NRRL B-11,219 | 18 | 50 | 2-Butanone |
| 14. *Methylobacterium organophilum* (CRL 26 R6) NRRL B-11,222 | 10 | — | 2-Butanone |

EXAMPLE 4

Microbiological Conversion of Alkanes to Ketones

A few of the newly discovered and isolated methylotrophic microorganisms of the invention were grown aerobically in a nutrient medium containing methane in the manner described in Example 1 and the washed cells were used to convert propane to acetone and butane to 2-butanone using the same procedure for the substrate oxidation as described in Example 1. The results of these experiments are shown in Table V.

TABLE V

Microbiological Conversion of Alkanes to Ketones

| Methylotrophic Microorganism Strain Identification | Conversion Rate to Ketone (μmoles/hr/mg Protein) | Substrate | Product |
|---|---|---|---|
| *Methylobacter chroococcum* (CRL M6) NRRL B-11,214 | 2.0 | Propane | Acetone |
| *Methylobacter bovis* (CRL M1Y) NRRL B-11,216 | 5.0 | Propane | Acetone |
| *Methylococcus capsulatus* (CRL M1) NRRL B-11,219 | 4.0 | Propane | Acetone |
| *Methylobacterium organophilum* (CRL R6) NRRL B-11,222 | 3.0 | Propane | Acetone |
| *Methylosinus trichosporium* (CRL 15 PM1) NRRL B-11,202 | 1.6 | Propane | Acetone |
| *Methylomonas rubrum* (CRL 20 PM6) NRRL B-11,211 | 3.5 | Propane | Acetone |
| *Methylobacter chroococcum* (CRL M6) NRRL B-11,214 | 1 | Butane | 2-Butanone |
| *Methylobacter bovis* (CRL M1Y) NRRL B-11,216 | 3 | Butane | 2-Butanone |
| *Methylococcus capsulatus* (CRL M1) NRRL B-11,219 | 2 | Butane | 2-Butanone |
| *Methylobacterium organophilum* (CRL R6) NRRL B-11,222 | 2.0 | Butane | 2-Butanone |
| *Methylosinus trichosporium* (CRL 15 PM1) NRRL B-11,202 | 1.0 | Butane | 2-Butanone |
| *Methylomonas methanica* (CRL 21 PM7) NRRL B-11,206 | 1.5 | Butane | 2-Butanone |
| *Methylocystis parvus* (CRL 18 PM4) NRRL B-11,203 | 1.0 | Butane | 2-Butanone |

EXAMPLE 5

Microbiological Conversion of n-Pentane and n-Hexane to Methyl Ketones by Cell-Suspensions of Methane-Grown Methylotrophic Microorganisms In this example, the procedure of Example 1 was repeated wherein a plurality of the methane-utilizing methylotrophic microorganisms of the invention were each aerobically grown in a methane-containing nutrient medium. The nutrients in the medium were the same as indicated in Example 1 wherein methane was used as the oxygenase enzyme inducer and major source of carbon and energy for growth. Following growth, the cells were harvested and washed as described in Example 1. The resting cells of the induced methane-grown methylotrophic microorganisms were then contacted with n-pentane or n-hexane under aerobic conditions in a buffered solution by the procedure in Example 1. The results of this series of experiments are shown in Table VI.

TABLE VI

Microbiological Conversion of n-Pentane and n-Hexane to Methyl Ketones By Cell-Suspensions of Methane-Grown Methane-Utilizing Methylotrophic Microorganisms

| Methylotrophic Microorganism Strain Identification[b] | Conversion Rate μmole/hr/mg protein[a] | |
|---|---|---|
| | n-Pentane to 2-Pentanone | n-Hexane to 2-Hexanone |
| *Methylosinus trichosporium* CRL 15 NRRL B-11,202 | 0.08 | 0.04 |
| *Methylomonas methanica* CRL 21 NRRL B-11,206 | 0.06 | 0.01 |
| *Methylobacter vinelandii* CRL M5Y NRRL B-11,218 | 0.04 | 0.01 |
| *Methylococcus capsulatus* CRL M1 NRRL B-11,219 | 0.15 | 0.08 |
| *Methylobacterium organophilum* CRL 26 NRRL B-11,222 | 0.18 | 0.02 |

[a]The products were identified by gas chromatography retention time comparisons with authentic standards. Analysis revealed that no further oxidation of the products occurred.
[b]The dry weight of the cells was about 0.2 g/100 ml of culture broth.

EXAMPLE 6

Microbiological Conversion of $C_3$–$C_6$ Linear Secondary Alcohols to Methyl Ketones by Cell-Suspensions of Methanol-Grown Methane-Utilizing Methylotrophic Microorganisms In this example, the procedure of Example 1 was repeated except that a plurality of the methane-utilizing methylotrophic microorganisms of the invention were each aerobically grown in a methanol-containing nutrient medium instead of a methane-containing medium. The nutrients in the medium were the same as indicated in Example 1 except that 0.4% v/v methanol was used as the alcohol dehydrogenase enzyme inducer and major source of carbon and energy for growth. Following growth the cells were harvested and washed as described in Example 1. The resting cells of the induced methanol-grown methylotrophic microorganisms were then contacted with a secondary alcohol under aerobic conditions in a buffered solution by the procedure described in Example 1. The results of this series of experiments are shown in Table VII.

TABLE VII

Microbiological Conversion of $C_3$–$C_6$ Secondary Alcohols to Methyl Ketones By Cell-Suspensions of Methanol-Grown Methane-Utilizing Methylotrophic Microorganisms

| Methylotrophic Microorganism Strain Identification[b] | Conversion Rates[a] μmoles/hr/mg protein | | | |
|---|---|---|---|---|
| | 2-Propanol to Acetone | 2-Butanol to 2-Butanone | 2-Pentanol to 2-Pentanone | 2-Hexanol to 2-Hexanone |
| *Methylosinus trichosporium* CRL 15 NRRL B-11,202 | 0.50 | 4.5 | 0.09 | 0.06 |
| *Methylocystis parvus* CRL 18 NRRL B-11,204 | 0.25 | 1.0 | 0.07 | 0.05 |
| *Methylomonas methanica* CRL M4P NRRL B-11,205 | 2.0 | 2.5 | 0.05 | 0.03 |
| *Methylomonas streptobacterium* CRL 17 PM3 NRRL B-11,208 | 0.67 | 2.0 | — | — |
| *Methylobacter chroococcum* CRL M6 NRRL B-11,214 | 1.0 | 1.4 | 0.08 | 0.02 |
| *Methylobacter bovis* CRL 19 NRRL B-11,217 | 0.40 | 1.8 | — | — |
| *Methylobacter vinelandii* CRL M5Y NRRL B-11,218 | 2.0 | 2.0 | 0.05 | 0.02 |
| *Methylococcus capsulatus* CRL M1 NRRL B-11,219 | 5.0 | 2.0 | 0.24 | 0.08 |
| *Methylococcus capsulatus* CRL 25 NRRL B-11,221 | 0.62 | 0.95 | — | — |
| *Methylobacterium organophilum* CRL 26 NRRL B-11,222 | 0.72 | 2.5 | 1.0 | 0.09 |

[a] The products were identified by gas chromatography retention time comparisons with authentic standards. Analysis also revealed that no further oxidation of the products occurred.
[b] The dry weight of the cells was about 0.2 g/100 ml culture broth.

EXAMPLE 7

Microbiological Oxidation of Cyclic Hydrocarbons

Methylobacter vinelandii (CRL M5Y NRRL B-11,218) was aerobically grown in a methane-containing nutrient medium in the manner described in Example 1 and the methane-grown washed cells were contacted under aerobic conditions with cyclohexane, benzene and toluene. Cyclohexane was found to be converted to cyclohexanol at a conversion rate of 1.5 μmoles/2 hr./mg. protein, whereas no oxidative conversion was detected in the case of benzene and toluene. Several of the other strains of the present invention which had been grown on methane did not produce any detectable cyclohexanol when the methane-grown cells were contacted with cyclohexane.

The newly discovered and isolated microorganisms of the present invention grow well in a nutrient medium under aerobic conditions containing carbon-containing compounds. When the carbon-containing compounds are oxygenase and/or alcohol dehydrogenase enzyme inducers, the resulting resting microbial cells and/or their enzyme preparations are capable of increasing the oxidative state of a plurality of oxidizable compounds (substrates). When methane is used as the oxygenase and/or alcohol dehydrogenase enzyme inducer and the major carbon and energy source, the resulting resting microbial cells and/or their enzyme preparations are capable of converting: $C_1$–$C_6$ n-alkanes to alcohols and ketones; $C_2$–$C_4$ alkenes to the corresponding 1,2-epoxides; $C_3$–$C_6$ linear secondary alcohols to the corresponding methyl ketones; and microbial cells from at least one strain was capable of converting cyclohexane to cyclohexanol.

This capability of carrying out these useful oxidative and/or alcohol dehydrogenating conversions has been shown above with respect to both the obligate and facultative methylotrophic microorganisms of the invention. In the case of either the obligate or facultative methylotrophic microorganisms of the present invention which have been aerobically grown in a nutrient medium containing a methyl-radical donating or precursor compound such as methanol, methylamine or methyl formate as the alcohol dehydrogenase enzyme inducer, the resulting resting microbial cells or their enzyme preparations are only capable of converting $C_3$–$C_6$ linear secondary alcohols to the corresponding methyl ketones. These induced enzymes are not capable of converting the $C_3$–$C_6$ alkanes to the corresponding methyl ketones and they are not capable of converting the $C_2$–$C_4$ alkenes to the corresponding 1,2-epoxides. In batch experiments of the epoxidation process using resting, methane-grown cells, the epoxidation reaction proceeds linearly for at least two hours. In the case of ketone production the reaction proceeded linearly for at least 4 hours. The oxidative enzyme system(s) of the methane- or methand-grown microorganisms of the present invention is inducible (by the methane or methanol) and the oxidation products accumulate extracellularly (i.e., after the reaction, the reaction mixtures were centrifuged and the desired oxidation product was only found in the supernatant fraction and not in the cell pellet).

As will be shown by the examples that follow, the methane-grown microbial cells and their enzyme preparations (including cell-free extracts) possess both oxygenase and alcohol dehydrogenase enzyme activity. It is believed that the methane itself induces the oxygenase enzyme activity and the methanol resulting from the oxidation of methane by the methylotrophic microorganism during growth induces the alcohol dehydrogenase enzyme. The induced oxygenase enzyme is responsible for converting the $C_3$–$C_6$ alkane to an intermediate oxidation product, and secondary alcohol, whereas the induced alcohol dehydrogenase enzyme dehydrogenates the secondary alcohol to the corresponding methyl ketone. Similarly, the monookygenase enzyme system induced by the methane growth substrate is at least partly responsible for catalyzing the conversion of the $C_2$–$C_4$ alkenes and butadiene to the corresponding 1,2-epoxides.

The Epoxidation System—Cell-Free Extracts

As previously indicated both the whole cells and the cell-free extracts containing the oxygenase enzyme activity of the methane grown methylotrophs may be used in the hydroxylation and epoxidation reactions in the presence of air. NADH and metal (iron or copper) may be added to enhance activity when the cell-free or pure enzyme preparations are used. In utilizing the cell-free enzyme system of the invention the enzyme preparations were prepared as follows.

Preparation of Cellular Fractions

Organisms were grown at 30° C. in 2.8 liter flasks containing 700 ml mineral salts medium as described in Example 1 with methane (methane and air, 1:1 parts by volume) as the sole carbon and energy source. Cells were harvested during exponential growth by centrifugation at 12,000×g. for 15 min. at 4° C. Cells were washed twice with 25 mM potassium phosphate buffer, pH 7.0 containing 5 mM $MgCl_2$. Cells were suspended in the same buffer. The cell suspensions at 4° C. were disintegrated by a single passage through a French Pressure cell (15,000 lb./in.$^2$) and centrifuged at 5000×g. for 15 min. to remove unbroken bacteria. The supernatant solution (crude extract) was then centrifuged at 40,000×g. for 30 min., yielding particulate P(40) and soluble S(40) fractions. The S(40) fraction was subsequently centrifuged at 80,000×g. for 60 min., yielding particulate P(80) and soluble S(80) fractions. The particulate fractions [P(40) and P(80)] were suspended in 25 mM potassium phosphate buffer, pH 7.0, containing 5 mM $MgCl_2$ and homogenized at 4° C.

Enzyme Assay

The oxidation of methane and propylene by particulate [(P)40 and(P)80] fractions and soluble [S(80)] fraction was measured at 30° C. by estimating the production of methanol and propylene oxide, respectively. The reaction mixtures contained in 1.0 ml: 150 mM potassium phosphate buffer, pH 7.0 containing 5 mM $MgCl_2$, 0.6 ml; 10 μmoles NADH, and cellular fraction.

Reaction mixtures were contained in 10 ml vials at 4° C. Vials were sealed with rubber caps. The gaseous phase in the vials was removed using vacuum and then was replaced with a gas mixture of methane or propylene and oxygen at a 1:1, v/v ratio. Oxidation of other gaseous n-alkanes and n-alkenes was examined as described above. For liquid substrates, 10 μl of substrate was used directly. Vials were then incubated at 30° C. on a rotary shaker at 200 RPM.

The products of epoxidation of n-alkenes and hydroxylation of n-alkanes were assayed by flame ionization gas chromatography using a stainless steel column (12'×⅛") packed with 10% Carbowax 20 M on 80/100 Chromosorb W and Porapak Q column. The column temperature was maintained isothermally at 120° C. The carrier gas flow rate was 30 ml/min. of helium. The various products were identified by retention time comparisons and co-chromatography with authenic standards.

Specific activities were expressed as μmoles of products formed per hour per mg. protein. Concentrations of protein in various fractions were determined by the method of Lowry et al., *J. Biol. Chem.*, 193: 265–275 (1951).

Distribution of n-Alkanes- and n-Alkenes-Oxidizing Activities in Cell-Fractions Three distinct groups of methane-utilizing organisms were selected to examine oxidation of n-alkanes ($C_1$–$C_4$) and n-alkenes ($C_2$–$C_4$) in cell-free systems. Cellular fractions were prepared from Type I obligate methane-utilizing organisms, Methylomonas sp. (CRL-17, NRRL B-11,208) and *Methylococcus capsulatus* (Texas, ATCC 19,069); Type II obligate methane-utilizing organisms, *Methylosinus trichosporium* (OB3b, NRRL B-11,196) and Methylosinus sp. (CRL-15, NRRL B-11,202); and a facultative methane-utilizing bacterium, Methylobacterium sp. (CRL-26, NRRL B-11,222).

Table VIII shows the distribution of the methane- and propylene-oxidizing activity in various fractions derived from these organisms. About 85–90% of the total activity was detected in the P(40) fraction and 10% was detected in the P(80) fraction. The soluble fraction S(80) did not contain any activity. The specific activities for the methane and the propylene oxidation in fractions P(40) and P(80) did not vary significantly in the various organisms examined (Table IX). Epoxidation of propylene and hydroxylation of methane were both dependent upon the presence of oxygen and NADH. NADPH or ascorbate and other electron carriers could also be utilized. Both reactions were linear during the first 15 min. as measured by detection of product by gas chromatography.

TABLE VIII

DISTRIBUTION OF PROPYLENE - AND METHANE-OXIDIZING ACTIVITIES IN CELL FRACTIONS OF METHYLOTROPHS

| | % Distribution in Cell Fraction | | | | | |
|---|---|---|---|---|---|---|
| | Propylene-Epoxidizing$^a$ Activity | | | Methane-Hydroxylating$^a$ Activity | | |
| Microorganism | P(40) | P(80) | S(80) | P(40) | P(80) | S(80) |
| Type 1 Obligate Methylotrophs | | | | | | |
| Methylomonas sp. (CRL-17, NRRL B-11,208) | 85 | 15 | 0 | 87 | 13 | 0 |
| *Methylococcus capsulatus* (Texas, ATCC 19,069) | 89 | 11 | 0 | 90 | 10 | 0 |
| Type II Obligate Methylotrophs | | | | | | |
| Methylosinus sp. (CRL-15, NRRL B-11,202) | 87 | 13 | 0 | 88 | 12 | 0 |
| *Methylosinus trichosporium* (CB3b, NRRL B-11,196) | 82 | 18 | 0 | 83 | 13 | 0 |
| Faculative Methylotroph Methylobacterium sp. (CRL-26, NRRL B-11,222) | 85 | 15 | 0 | 82 | 18 | 0 |

$^a$Reactions were carried out as described in Example 1. The product of reaction was estimated by gas chromatography after 5, 10 and 15 min. of incubation of reaction mixture at 30° C. on a rotary shaker.

TABLE IX

THE RATE OF METHANE HYDROXYLATION - AND PROPYLENE-EPOXIDATION IN THE CELL-FRACTIONS OF METHYLOTROPHS

| | Cell Fraction | | | | | |
|---|---|---|---|---|---|---|
| | Propylene-Oxidizing$^a$ Activity | | | Methane-Oxidizing$^a$ Activity | | |
| Microorganism | P(40) | P(80) | S(80) | P(40) | P(80) | S(80) |
| Type 1 Obligate Methylotroph | | | | | | |
| Methylomonas sp. (CRL-17, NRRL B-11,208) | 2.2 | 2.0 | 0 | 2.9 | 2.7 | 0 |
| *Methylococcus capsulatus* (Texas, ATCC 19,069) | 2.6 | 2.0 | 0 | 3.8 | 3.9 | 0 |
| Type II Obligate Methylotroph | | | | | | |

TABLE IX-continued

THE RATE OF METHANE HYDROXYLATION AND PROPYLENE-EPOXIDATION IN THE CELL-FRACTIONS OF METHYLOTROPHS

| | Cell Fraction | | | | | |
|---|---|---|---|---|---|---|
| | Propylene-Oxidizing[a] Activity | | | Methane-Oxidizing[a] Activity | | |
| Microorganism | P(40) | P(80) | S(80) | P(40) | P(80) | S(80) |
| Methylosinus sp. (CRL-15, NRRL B-11,202) | 3.8 | 3.7 | 0 | 4.8 | 4.2 | 0 |
| Methylosinus trichosporium (OB3b, NRRL B-11,196) | 2.8 | 2.5 | 0 | 3.1 | 3.0 | 0 |
| Faculative Methylotroph Methylobacterium sp. (CRL-26, NRRL B-11,222) | 1.2 | 1.1 | 0 | 2.7 | 2.8 | 0 |

[a] Reactions were carried out as described in Example 1. The product of the reaction was estimated by gas chromatography after 5, 10 and 15 min. of incubation of reaction mixtures at 30° C. on a rotary shaker. The rate of oxidation is expressed as $\mu$ moles of product formed per hr. per mg. of protein.

The particulate fractions [P(40) and P(80)] from various organisms also catalyzed the epoxidation of other n-alkenes (ethylene, 1-butene, and 1,3-butadiene) to the corresponding 1,2-epoxides and the hydroxylation of methane and ethane to the corresponding alcohols. Table X shows the race of oxidation of various n-alkanes and n-alkenes by the P(40) particulate fraction of Methylosinus sp. (CRL-15, NRRL B-11,202). The product of oxidation was identified by gas chromatography after incubating P(40) fraction with various substrates at 30° C. for 10 min.

TABLE X

OXIDATION OF n-ALKENES AND n-ALKANES BY P(40) PARTICULATE FRACTION OF METHYLOSINUS SP. (CRL-15, NRRL B-11,202)

| Substrate | Product | Rate of Product Formation[a] ($\mu$moles/hr/mg of protein) |
|---|---|---|
| Ethylene | Ethylene Oxide | 1.27 |
| Propylene | Propylene Oxide | 4.1 |
| 1-Butene | Epoxy butane | 2.18 |
| Butadiene | Epoxy butene | 0.63 |
| 1-Pentene | — | 0 |
| Methane | Methanol | 4.8 |
| Ethane | Ethanol | 3.2 |

[a] Reactions were carried out as described in Example 1. The product of the reaction was estimated by gas chromatography after 5, 10, and 15 min. of incubation of reaction mixture at 30° C. on a rotary shaker.

Methylosinus sp. (CRL-15, NRRL B-11,202) was selected for further studies on the influence of various environmental factors on the methane- and propylene-oxidizing activities in cell-free systems.

Effect of Particulate Fraction Concentration

The effect of the P(40) particulate fraction concentration on the hydroxylation of methane and epoxidation of propylene was examined. The production of methanol and propylene oxide was directly dependent upon the concentration of particulate fraction ranging from 1–6 mg. of protein per ml. The rate of reaction was decreased upon further increasing the particulate protein concentration to 8 mg./ml.

Time Course of Reactions

The rate of formation of methanol and propylene oxide by hydroxylation of methane and epoxidation of propylene respectively, by the P(40) particulate fraction of Methylosinus sp. (CRL-15, NRRL B-11,202) was linear with time up to 15 minutes.

Effect of pH

The effect of pH on the hydroxylation of methane and epoxidation of propylene by the P(40) particulate fraction of Methylosinus sp. (CRL-15, NRRL B-11,202) was examined by estimating the amount of methanol and propylene oxide formed after 10 min. incubation of reaction mixtures. The optimum pH for both hydroxylation of methane and epoxidation of propylene was found to be 7.0. In carrying out these tests the reactions were carried out as described in Example 1. The product of reaction was estimated by gas chromatography after 5, 10 and 15 minutes of incubation of reaction mixture at 30° C. on a rotary shaker. 100% activity equals 4.8 and 4.1 $\mu$moles of methanol or propylene oxide formed respectively, per hour, per mg protein.

Effect of Temperature

The effect of temperature on the production of methanol and propylene oxide by the P(40) particulate fraction of Methylosinus sp. (CRL-15, NRRL B-11,202) was examined after incubation of reaction mixtures for 10 min. at various temperatures. The optimum temperature for epoxidation of propylene and hydroxylation of methane was found to be 35° C. In carrying out these tests the reactions were carried out as described in Example 1. The product of reaction was estimated by gas chromatography after 5, 10 and 15 minutes of incubation of reaction mixture at 30° C. on a rotary shaker. 100% activity equals 5.0 and 4.2 $\mu$moles of methanol and propylene oxide formed respectively, per hour per mg of protein.

Effect of Storage

It was noted that both the activity for hydroxylation of methane and the epoxidation of propylene by the P(40) particulate fraction of Methylosinus sp. (CRL-15, NRRL B-11,202) decreased simultaneously when stored at refrigerator (0°–4° C.) temperature. In carrying out these tests the reactions were carried out as described in Example 1. The product of reaction was estimated by gas chromatography after 5, 10 and 15 minutes incubation of the reaction mixture at 30° C. on a rotary shaker. 100% activity equals 4.8 and 4.1 $\mu$moles of methanol and propylene oxide formed respectively per hr. per mg. of protein.

Effect of Inhibitors

It has been reported that the oxidation of methane by cell suspensions of methane-utilizing bacteria was inhibited by various metal-binding or metal-chelating agents (Patel et al., *J. Bacteriol.* 126: 1017–1019 (1976)). Hence, the effect of inhibitors on methane- and propylene-oxidizing activities by the P(40) particulate fraction of Methylosinus sp. (CRL-15, NRRL B-11,202) was examined. The production of methanol and propylene oxide was inhibited by various metal-binding compounds with different ligand combinations, i.e., nitrogen-nitrogen ($\alpha,\alpha$-bipyridyl), oxygen-nitrogen (8-hydroxyquinoline) and sulfur-nitrogen (thiourea, thiosemicarbazide) as shown in Table XI. This suggests the involvement of metal ion(s) in the oxidation of both hydroxylation of methane, and epoxidation of propylene. Similarly, as shown in Table XIa these compounds also inhibit the hydroxylation of methane and epoxidation of propylene when using cell-containing enzyme preparations.

TABLE XI
EFFECT OF INHIBITOR ON THE ACTIVITY FOR EPOXIDATION OF PROPYLENE AND HYDROXYLATION OF METHANE BY METHYLOSINUS SP. (CRL-15, NRRL B-11,202)

| Inhibitor | Concentration (M) | % Inhibition[a] Propylene-Epoxidizing Activity | Methane-Hydroxylating Activity |
|---|---|---|---|
| Control | — | 0 | 0 |
| α,α-Bipyridyl | $10^{-3}$ | 98 | 99 |
| 1,10-Phenanthroline | $10^{-3}$ | 93 | 90 |
| Potassium cyanide | $10^{-3}$ | 98 | 100 |
| Thiosemicarbazide | $10^{-3}$ | 97 | 100 |
| Thiourea | $10^{-3}$ | 98 | 98 |
| 8-Hydroxyquinoline | $10^{-3}$ | 75 | 80 |

[a]Reactions were carried out as described in Example 1. The product of the reaction was estimated by gas chromatography after 5, 10, and 15 min. incubation of the reaction mixture at 30° C. on a rotary shaker. The uninhibited rates of methane and propylene oxidation were 4.5 and 4.1 μmoles of methanol and propylene oxide formed, respectively, per hr. per mg. of protein in P(40) fraction of Methylosinus sp. (CRL-15, NRRL B-11,202).

Effect of Metals

Since the methane mono-oxygenase from methane-utilizing bacteria is a copper or iron-containing protein (Tonge et al., *J. Biochem.*, 161: 333–344 (1977)), we have examined the effect of copper and iron salts on the oxidation of methane and propylene by the P(40) particulate fraction of Methylosinus sp. (CRL-15, NRRL B-11,202). The rate of hydroxylation of methane to methanol and epoxidation of propylene to propylene oxide was increased twofold in the presence of added copper salts (Table XII).

Substrate Competition Experiments

The hydroxylation of methane and the epoxidation of propylene by particulate fractions of methane-utilizing bacteria required oxygen and NADH. The question of whether the same or a similar enzyme was involved in the oxidation of both substrates was examined by substrate competition experiments. The experiment consisted of determining the effect of methane on the oxidation of propylene to propylene oxide by the P(40) particulate fraction of Methylosinus sp. (CRL-15, NRRL B-11,202). As shown in Table XIII, there was a reduction in the amount of propylene oxide formed in the presence of methane. Hence, methane inhibited the conversion of propylene to propylene oxide, presumably by competing for the available enzymatic site.

TABLE XIII
EFFECT OF METHANE ON PROPYLENE EPOXIDIZING ACTIVITY BY P(40) PARTICULATE FRACTION OF METHYLOSINUS SP. (CRL-15, NRRL B-11,202)

| Substrate | Propylene Oxide Produced[a] μmoles/hr/mg. protein |
|---|---|
| Propylene | 4.3 |
| Propylene + Methane (1:1, v/v) | 1.8 |
| Methane | 0 |

[a]Reactions were carried out as described in Example 1. The product of the reaction was estimated by gas chromatography after 5, 10 and 15 min. of incubation of the reaction mixture at 30° C. on a rotary shaker.

Similarly, methane affects the epoxidation of propylene from cell-suspensions of methane-grown *Methylosinus trichosporium* OB3b (NRRL B-11,196) as shown in Table XIIIa.

TABLE XIII[a]
EFFECT OF METHANE ON THE EPOXIDATION OF PROPYLENE[a]

| Composition of Gaseous Phase | Propylene Oxide Formed (μmoles) | % Inhibition |
|---|---|---|
| Propylene + Helium + $O_2$ (25:25:50 v/v) | 1.6 | 0 |
| Propylene + Methane + $O_2$ | 0.8 | 50 |

TABLE XI[a]
Effect of Inhibitors on the Epoxidation of Propylene and the Hydroxylation of Methane

| | % Inhibition | | | | | |
|---|---|---|---|---|---|---|
| | *Methylosinus trichosporium* OB3b *capsulatus* (NRRL B-11,196) | | *Methylococcus organophilum* (CRL M1, NRRL B-11,219) | | *Methylobacterium* (CRL 26, NRRL B-11,222) | |
| Inhibitor | Epoxidation | Hydroxylation | Epoxidation | Hydroxylation | Epoxidation | Hydroxylation |
| Thiourea | 100 | 100 | 100 | 100 | 100 | 100 |
| 1,10-phenathroline | 90 | 92 | 95 | 95 | 90 | 90 |
| α,60-Bipyridyl | 100 | 90 | 100 | 100 | 100 | 100 |
| Imidazole | 95 | 90 | 95 | 95 | 100 | 100 |
| Potassium cyanide | 100 | 100 | 100 | 100 | 95 | 95 |

The reactions were conducted as described in Example 1. The products were estimated by gas chromatography after 1 hour of incubation at 30° C. Each inhibitor was added at a final concentration of 1 mM.

TABLE XII
EFFECT OF METALS ON THE ACTIVITY FOR EPOXIDIZING PROPYLENE AND HYDROXYLATING METHANE BY METHYLOSINUS SP. (CRL-15, NRRL B-11,202)

| Metal | Concentration (M) | Propylene-Oxidizing[a] Activity (μmoles/hr/mg protein) | Methane-Oxidizing[a] Activity (μmoles/hr/mg protein) |
|---|---|---|---|
| Control | — | 4.5 | 4.0 |
| Ferric Chloride | $10^{-3}$ | 5.8 | 4.8 |
| Ferrous Sulfate | $10^{-3}$ | 5.9 | 4.8 |
| Cuprous Chloride | $10^{-3}$ | 9.2 | 7.2 |
| Cupric Sulfate | $10^{-3}$ | 9.0 | 7.1 |

[a]Reactions were carried out as described in Example 1. The product of the reaction was estimated by gas chromatography after 5, 10 and 15 min. of incubation of the reaction mixture at 30° C. on a rotary shaker. The rates of oxidation were expresed as μmoles of product formed per hr. per mg. of protein in P(40) fraction of Methylosinus sp. (CRL-15, NRRL B-11,202).

TABLE XIII[a-continued]
EFFECT OF METHANE ON THE EPOXIDATION OF PROPYLENE[a]

| Composition of Gaseous Phase | Propylene Oxide Formed (μmoles) | % Inhibition |
|---|---|---|
| (25:25:50 v/v) | | |

[a]The reactions were conducted as described in Example 1 except that various gaseous compositions were used to maintain a constant propylene partial pressure. Cell-suspensions of methane-grown *Methylosinus trichosporium* OB3b (NRRL B-11,196) (3.6 mg.) were used. Propylene oxide was estimated by gas chromatography after 15 minutes of the incubation.

Stoichiometry of Propylene and Methane Oxidation

The particulate P(40) fraction of Methylosinus sp. (CRL-15, NRRL B-11,202) was used to determine the stoichiometry of hydroxylation and epoxidation reactions. The stoichiometry of methane or propylene-dependant NADH oxidation, oxygen consumption and product formation was approximately 1:1:1 Table XIV. This is consistent with methane or propylene oxygenation being catalyzed by a mono-oxygenase.

TABLE XIV
STOICHIOMETRY OF PROPYLENE EPOXIDATION AND METHANE HYDROXYLATION BY P(40) PARTICULATE FRACTION OF METHYLOSINUS SP. (CRL-15, NRRL B-11,202)[a]

| Substrate (μmoles) | Product Formed (μmoles) | NADH Oxidized (μmoles) | $O_2$ Consumed (μmoles) |
|---|---|---|---|
| Propylene 5.0 | Propylene Oxide 4.5 | 5.0 | 4.8 |
| Methane 5.0 | Methanol 4.2 | 4.8 | 4.6 |

[a]Under identical condition of reaction, the estimation of NADH oxidized was carried out spectrophotometrically, the estimation of oxygen consumed was measured polarographically, and estimation of product formed was carried out by gas chromatography.

As a comparison the stoichiometry of the epoxidation of propylene by a cell-suspension of *Methylosinus trichosporium* OB3b (NRRL B-11,196) was determined as follows. The reaction mixture (3.0 ml.) contained 0.05 M sodium phosphate buffer, pH 7.0 and 3.6 μmoles of propylene. The reaction was initiated by the injection of 0.1 ml. of cell-suspension (3.1 mg. protein). A correction was made for the endogenous consumption of oxygen. The amount of oxygen consumed during the reaction (3 min.) was determined polarographically with a Clark oxygen electrode. The propylene consumed and the propylene oxide formed was estimated by gas chromatography. The propylene consumed was 0.29 μmoles, the oxygen consumed was 0.30 μmoles and the propylene oxide formed was 0.28 μmoles.

To further demonstrate that the enzyme activity is in the particulate fraction (not in the supernatant) the following experiments were carried out. Cells of methane-grown *Methylococcus capsulatus* (CRL M1, NRRL B-11,219) were obtained by the method of Example 1. The crude extract after 10,000×g. centrifugation of sonically disrupted (3×50 sec., Wave Energy Ultrasonic Oscillator, Model W 201) was found to have no activity for either epoxidation or hydroxylation. However, when the cells were disrupted by passing twice through a French pressure cell (1000 Kg. pressure), both activities were found in the crude extract after 10,000×g. centrifugation. All of the activity in the crude extract was collected as a particulate fraction by further centrifugation of the crude extract as 40,000×g. for 90 min. at 4° C. NADH stimulated both the epoxidation and the hydroxylation reactions as shown in Table XV.

TABLE XV
EPOXIDATION AND HYDROXYLATION ACTIVITIES IN CELL-FREE FRACTION OF *METHYLOCOCCUS CAPSULATUS* (CRL M1, NRRL B-11,219)[a]

| | Oxidation Rate (nmoles)/30 min/assay) | |
|---|---|---|
| Cell-Free Fractions | Epoxidation of Propylene | Hydroxylation of Methane |
| (1) Particulate fraction (10,000 × g.−40,000 × g.) | 750 | 500 |
| (1) + NADH | 900 | 650 |
| (2) Supernatant fraction of 40,000 × g. | 0 | 0 |
| (2) + NADH | 0 | 0 |

[a]The cells were disrupted by French Press as described above. NADH (2.5 μmoles) was added into the reaction mixture where indicated. The amount of protein in the particulate fraction and the 40,000 × g. supernatant fraction used was 1 mg. and 2.5 mg., respectively. Each assay contained 0.5 ml. reaction mixture.

SUMMARY OF EPOXIDATION SYSTEM

Both the system of *Pseudomonas aeruginosa* demonstrated by Van der Linden, Biochim. Biophys. Acta., 77:157–159 (1963) and the system of *Pseudomonas oleovorans*, Abbott and Hou, Appl Microbiol., 26: 86–91 (1973) epoxidized liquid 1-alkenes from $C_6$ to $C_{12}$, but not gaseous alkenes.

The present invention provides for the epoxidation of ethylene, propylene, 1-butene and butadiene by cell suspensions of all three distinct groups of methane-utilizing bacteria. The epoxidation of alkenes and the hydroxylation of methane were not found under anaerobic conditions or in methanol-grown cells, suggesting that the enzyme system is inducible. The product 1,2-epoxides accumulated extracellularly. The nonenzymic degradation of propylene oxide in the assay system disclosed was not significant even after a prolonged incubation time. Van der Linden, supra, demonstrated the production of 1,2-epoxyoctane from 1-octene by heptane-grown cells of Pseudomonas sp. and also stated that the epoxide was not further oxidized enzymatically. However, May and Abbott, Biochem. Biophys. Res. Commun., 48:1230–1234 (1972) and J. Biol. Chem., 248: 1725–1730 (1973) reported that when 1-octene was supplied as a substrate to the ω-hydroxylation enzyme system of *P. oleovorans*, both 8-hydroxyl-1-octene and 1,2-epoxyoctane were formed. In addition, Abbott and Hou, supra, found that the methyl group of the latter compound was also susceptible to hydroxylation. The present results obtained from the studies of viable cell suspensions of the methane-utilizing bacteria, however, indicated that propylene oxide was not further metabolized enzymatically.

Van der Linden, supra, showed that the epoxide accumulation from 1-octene by *Pseudomonas aeruginosa* was accompanied by the metabolism of a large quantity of 1-octene via methyl group epoxidation. In the epoxidation of propylene by cell suspensions of methane-utilizing bacteria, however, no formation of 3-hydroxy propene-1 was detected.

Both the epoxidation of the $C_2$–$C_4$ 1-alkenes and the hydroxylation of methane with the cell suspensions were inhibited by various metal-binding and metal-chelating agents, indicating the involvement of metal(s)-containing enzyme system(s). The similar extent of inhibition for both propylene and methane oxidation (Table XIa) indicated that the epoxidation and hydroxylation reaction may be catalyzed by the same or a similar enzyme system. The epoxidation of propylene to propylene oxide by a cell suspension of methane-grown strain *Methylococcus capsulatus* NRRL B-11,219 was inhibited (50%) in the presence of the hydroxylation substrate, methane (Table XV). This clearly suggests a comparison between the hydroxylation substrate and the epoxidation substrate for a single enzyme system. It is likely that the methane mono-oxygenase enzyme system catalyzes both the epoxidation of alkene and the hydroxylation of methane. May and Abbott publications, supra, have reported that the ω-hydroxylation system from *Pseudomonas oleovorans* catalyzed both the epoxidation of 1-octene and the hydroxylation of n-octane.

The optimum conditions for the in vivo epoxidation of propylene by cell suspensions of the three distinct groups of methane-utilizing bacteria are quite similar. The pH optima were around 6–7 and the temperature optimum was around 35° C. The apparent decrease in epoxidation above 40° C. may be due to both the instability of the mono-oxygenase system and the volatility of the product propylene oxide. (b.p. 35° C.).

Both the hydroxylation and epoxidation activities are located in the cell-free particulate fraction precipitated between $10,000 \times g$. and $80,000 \times g$. centrifugation. Tonge et al., *Biochem. J.*, 161: 333–344 (1977) and *FEBS Lett.*, 58: 293–299 (1975) have reported the purification of a membrane-bound methane mono-oxygenase from the particulate fraction (sedimented between $10,000 \times g$. and $150,000 \times g$. centrifugation) of *Methylosinus trichosporium* OB3b. Recently, but subsequent to our discoveries Colby et al., *Biochem. J.*, 165: 395–402 (1977) demonstrated a unique soluble methane monooxygenase from *Methylococcus capsulatus* (Bath strain) which catalyzes the oxidation of n-alkanes, n-alkenes, ethers and alicyclic, aromatic and heterocyclic compounds. The strains from the three distinct groups of methane-utilizing bacteria that we have examined all catalyze the epoxidation of gaseous alkenes ($C_2$–$C_4$) and the hydroxylation of gaseous alkanes ($C_1$–$C_4$). Also, we unexpectedly found the enzyme activity is in the particulate fraction (i.e., the material which sediments when the supernatant after centrifuging broken cells at $10,000 \times g$. for 30 minutes is centrifuged for 1 hour at $10,000 \times g$. or greater), not the soluble fraction (i.e., the supernatant after centrifuging broken cells at $80,000 \times g$. or greater for 1 hour.

Differential centrifugation of broken-cell suspensions of Methylomonas sp. (CRL-17, NRRL B-11,208) and *Methylococcus capsulatus* (Texas ATCC 19,069), (Type I obligate methlotrophs); Methylosinus sp. (CRL-15, NRRL B-11,202) and *Methylosinus trichosporium* (OB3b, NRRL B-11,196) (Type II obligate methylotrophs); and Methylobacterium sp. CRL-26, NRRL B-11,222) (a facultative methylotroph) has yielded cell-free particulate fractions that catalyzed the hydroxylation of n-alkanes and the epoxidation of n-alkenes. Both activities mainly resided in the P(40) fraction and were dependent upon the presence of oxygen, as well as electron carrier, e.g., NADH.

The hydroxylation of methane to methanol and the epoxidation of propylene to propylene oxide catalyzed by the P(40) particulate fraction of Methylosinus sp. (CRL-15, NRRL B-11,202) have similar pH and temperature optima. Both activities were lost simultaneously during storage of the P(40) particulate fraction at refrigerator temperature.

The hydroxylation of methane and the epoxidation of propylene with the cell-free extracts were strongly inhibited by various metal-binding or metal-chelating agents (Table XI). The rate of both reactions were increased twofold in the presence of copper or iron salts (Table XII). This suggests the involvement of a metal-containing enzyme system in the oxidation of both substrate. These results, and the stoichiometry of the hydroxylation and the epoxidation reactions indicate that both reactions may be catalyzed by the same metal-containing monooxygenase system. The fact that conversion of propylene to propylene oxide was inhibited by methane support this proposition.

It has been reported that the cell-free particulate fractions derived from *Methylococcus capsulatus* (Texas) (Ribbons et al., *J. Bacteriol.*, 122: 1351–1363 (1975)), *Methylomonas methanica* (Ferenci et al., *J. Gen. Microbiol.*, 91: 79–91 (1975)) and *Methylosinus trichosporium* (OB3b) (Tonge et al., *Biochem. J.*, 161: 333–344 (1977)) catalyzed oxygen- and NADH-dependent oxidation of methane, ethane, propane, butane, and carbon monoxide. The oxidation of methane by particulate fractions of these organisms was inhibited by various metal-binding or metal-chelating agents. However, epoxidation of n-alkenes was not reported for these organisms.

The methane monooxygenase from *Methylosinus trichosporium* (OB3b, NRRL B-11,196) has been purified and shown to be consisting of three components: a soluble CO-binding cytochrome c, a copper-containing protein (methane monooxygenase), and a small molecular weight protein (Tonge et al., 1977, supra).

In contrast to the above organisms, Colby et al., supra have reported the unique soluble methane monooxygenase activity from *Methylococcus capsulatus* (Bath). The oxidation of methane by the soluble fraction of this organism was not inhibited by various metal-binding agents. Recently, Colby and Dalton (Biochem. J., 171: 461–468 (1978)) resolved the methane monooxygenase of *Methylococcus capsulatus* (Bath) into three components and identified one of the components as an iron-containing flavoprotein.

The methane-oxidizing activities from the methylotrophic bacteria described above is in the particulate fraction and different from the soluble activity of *Methylococcus capsulatus* (Bath) disclosed by Colby et al.

Van der Linden (1963, supra) demonstrated the production of 1,2-epoxides from 1-octene by heptene-grown resting cells of Pseudomonas sp. Epoxides were not detected as products of alkane metabolism and were not oxidized by Pseudomonas sp. Thus, the role of epoxides in alkane metabolism is uncertain. Van der Linden postulated that the enzyme system that forms epoxides may be the same as the system that catalyzes the initial oxidation of alkanes. Cardini and Jurtshuk (*J. Biol. Chem.*, 245: 2789–2796 (1970)) found that a cell-free extract of a Corynebacterium sp. carried out the oxidation of 1-octene to epoxyoctane in addition to hydroxylation of octane to octanol. McKenna and Coon (*J. Biol. Chem.*, 245: 3883–3889 (1970)) isolated an enzyme system from *Pseudomonas oleovorans* that catalyzed the hydroxylation of n-alkanes ($C_6$–$C_{12}$) and fatty acids. Subsequently, Abbott and Hou, supra and May and Abbott, supra reported that the enzyme system from *Pseudomonas oleovorans* also catalyzed the epoxidation of 1-alkenes in addition to the hydroxylation reactions. The enzyme systems from Pseudomonas and Corynebacterium sp. catalyzed epoxidation of $C_6$–$C_{12}$ n-alkenes. Epoxidation of $C_2$–$C_5$ n-alkenes was not catalyzed by the Pseudomonas enzyme systems.

We have unexpectedly demonstrated that the three distinct groups of methane-oxidizing bacteria catalyze the hydroxylation of n-alkanes ($C_1$–$C_4$) as well as the epoxidation of n-alkenes ($C_2$–$C_4$). Furthermore, the hydroxylation and the epoxidation reactions are catalyzed by the same or a similar NADH-dependent monooxygenase.

In addition to methylotrophic bacteria, other microorganisms can be used to carry out the epoxidation of $C_2$–$C_4$ alkenes. These include bacteria, fungi and yeast which grow on short chain alkanes. The methylotrophic bacteria (obligate or facultative) or the other microorganisms are grown either on methane as a sole source of carbon, or on another carbon compound (in the presence of methane or another inducer), and the cells, or enzymes derived therefrom, may be used in the process of the present invention.

ALCOHOL OXIDATION SYSTEMS

As shown and discussed above (Table IX) resting-cell suspensions of methane- and methanol-grown microbial cells oxidized (dehydrogenated) $C_3$–$C_6$ secondary alcohols to their corresponding methyl ketones. The product methyl ketones accumulated extracellularly as determined by analysis of the supernatant of the centrifuged reaction mixture. Control experiments with heat-killed cells indicated that the methyl ketones were produced enzymatically. In these tests, secondary alcohol dehydrogenase (SADH) activity was found in all of the $C_1$-utilizers tested. Further tests have shown that SADH activity was found in cell suspensions of methanol-grown or methylamine-grown microorganisms. However, the SADH does not appear to be a constitutive enzyme since the SADH enzyme activity was not found in succinate-grown facultative $C_1$-utilizers.

To prepare the cell-free secondary alcohol dehydrogenous (SADH) system, the washed cells were disrupted with a Wave Energy Ultrasonic Oscillator, Model W201 (Wave Energy System, Inc., Newtown, Pa.) and centrifuged at 20,000×g. for 30 minutes. The clear supernatant contained the SADH activity. The enzyme activity was measured with a fluorescence spectrophotometer (Perkin Elmer, Model MPF 44A) by following the formation of reduced NAD (EX 340 nm, Em 460 nm). The formation of reduced NAD was also followed with an absorption spectrophotometer at 340 nm. The assay system (3 ml.) contained: potassium phosphate buffer pH 7.0; 150 μmol.; NAD 1 μmol.; a given amount of enzyme preparation; and secondary alcohol 10 μmol. The reaction was started by the addition of substrate. One unit of enzyme activity represents the reduction of one μmole NAD per minute. Protein concentrations were determined by the Lowry method as referenced above.

The following summarizes tests conducted on the optimal conditions for the production of methyl ketones from $C_3$–$C_6$ sec. alcohols. It will be understood that these were the optimal conditions found and the invention is not meant to be bound by them. Conversions can still be obtained by deviating from optimum indicated below, but with lower yields and conversions.

Time Course

The production of 2-butanone from 2-butanol reached a maximum after 14 hours of incubation in batch experiments in all the microorganisms tested. The amount of 2-butanone did not decline after 30 hours of incubation. The rate of 2-butanone production was linear for the first 4 hours. Therefore, the production of 2-butanone was measured within this interval whenever the effect of a variable was tested.

pH

The effect of pH on the production of 2-butanone was studied with tris (hydroxymethyl) amino methane-HCl buffer (0.05 M) for pH values of 8.0 to 10.0, and 0.05 M potassium phosphate buffer for values from 5.0 to 8.0. A pH around 8.0 was found to be the optimum for 2-butanone formation in all the microorganisms tested. Of the new strains, *Methylobacterium organophilum* CRL 26 (NRRL B-11,222), showed high activity at both 8 and 9. The yeast cells appeared less affected by pH in the production of 2-butanone.

Temperature

The temperature optimum for the production of 2-butanone by cell-suspensions was about 35° C. except for the yeast culture, which had an optimum of about 40° C.

Substrate Concentration

Various concentrations of 2-butanol were added to cell-suspensions of yeast and of strain Pseudomonas sp. ATCC 21439. The production of 2-butanone was assayed after 35 min. of incubation. The amount of 2-butanone produced was dependent on the amount of substrate initially added. A 2-butanol concentration of about 50 μmoles supported maximum 2-butanone production.

Cell Concentration

The cell concentration also has an influence on the rate of 2-butanone production. The amount of 2-butanone accumulated after 2 hours of incubation increased linearly as the cell concentration was increased by to about 12 mg./0.5 ml. for yeast and for *Methylococcus capsulatus* CRL M1 (NRRL B-11,219) and about 17 mg./0.5 ml. for strains *Methylobacterium organophilum* CRL 26R₆ (NRRL B-11,222), *Methylosinus trichosporium* OB3b (NRRL B-11,196) and Pseudomonas sp. ATCC 21.439.

Product Inhibition and Further Oxidation

Examination of the time course of 2-butanone production revealed that the rate decreased after 4 hours of incubation, suggesting, among other possibilities, either product inhibition or further oxidation of 2-butanone. To test these possibilities, 8 μmoles of 2-butanone was added to viable or heat-killed cell suspensions and incubated under the conditions described above for producing the 2-butanone. No decline was observed in 2-butanone concentration in all the heat-killed cell suspensions, but 2-butanone slowly disappeared in the presence of viable cells of all the strains tested. When 2-butanol (5 μl/0.5 ml. reaction mixture) was added to viable cell-suspensions along with the exogenously supplied 2-butanone, a net increase in 2-butanone production was detected. The reaction rates were identical to those where the secondary alcohol was initially converted to the methyl ketone and were not affected by the presence of the exogenously supplied 2-butanone. These data indicate that there is no product inhibition in the production of 2-butanone. A small amount of further oxidation of 2-butanone by viable cell-suspensions was observed. The decrease in 2-butanone production rate after 4 hours of incubation may be due to the depletion of other requirement(s), e.g., a cofactor(s).

Inhibition Studies

The production of 2-butanone from 2-butanol by cell suspensions of the strains tested was inhibited by metal-chelating agents such as 1, 10-phenanthroline and α,α-dipyridyl. However, the activity was not inhibited by sodium cyanide or thiourea which suggests metal involvement for the enzyme. The results of the inhibition tests are shown in Table XVI.

TABLE XV

EFFECT OF METAL-CHELATING AGENTS AND OTHER INHIBITORS ON THE PRODUCTION OF 2-BUTANONE BY CELL SUSPENSIONS OF METHANOL-GROWN *METHYLOCOCCUS CAPSULATES*CRL M1 (NRRL B-11,219)

| Metal-Chelating Agents | Concentration | Inhibition (%) |
|---|---|---|
| Sodium cyanide | 1 mM | 0 |
| Sodium azide | 1 mM | 10 |
| EDTA | 1 mM | 70 |
| 1,10-phananthroline | 1 mM | 95 |
| α,α-bipyridyl | 1 mM | 75 |
| Thiourea | 1 mM | 0 |

Substrate Specificity

The substrate specificity for the oxidation of $C_3$–$C_6$ secondary alcohols by the strains of $C_1$-utilizers was studied. Among the secondary alcohols, 2-propanol and 2-butanol were oxidized at higher rates; 2-pentanol, 2-hexanol, and 2-heptanol were oxidized at a much slower rate. The oxidation products of these secondary alcohols were the corresponding methyl ketones, as determined by GC retention time comparisons with authentic standards.

Cell-Free System

Cell-free soluble extracts from sonically disrupted cells of new strains and known strains also oxidized 2-butanol to 2-butanone. These results are shown in Table XVII. However, all of the cell-free systems tested required the addition of a cofactor, NAD, for its activity. Other cofactors tested (including NAD(P)H, NADP, phenazine methosulfate, GSH, FAD, potassium ferricyanide, and dichlorophenol indophenol) were not effective. The stoichiometry for the consumption of 2-butanol, the reduction of NAD, and the formation of 2-butanone was obtained for Pseudomonas sp. ATCC 21,439 as shown in Table XVIII. This is the first report of an NAD-dependent secondary alcohol dehydrogenase.

The experimental procedure for the tests reported in Table XVII were as follows: 1 mg protein of crude extract was added into a 0.5 ml. 0.05 M phosphate buffer (pH 7.0) in a 10-ml. vial. One μmol NAD and 10 μmol 2-butanol was added, and the vial was sealed with a rubber cap to minimize evaporation. The reaction mixture was incubated at 30° C. on a water bath. A 3 μl sample was removed with a syringe at 15 min. of incubation and was assayed with g.l.c. Catalytic activity was also assayed by fluorescence spectrophotometry. Data obtained from both g.l.c. and fluorescence spectrophotometric assays agreed with each other. Comparable conversions (as reported in Table XXVII) for extracts derived from $CH_3NH_2$ and $HCOOCH_3$ grown microbes were also obtained.

TABLE XVII

OXIDATION OF 2-BUTANOL TO 2-BUTANONE BY CELL-FREE SOLUBLE EXTRACTS OF C1-UTILIZING MICROBES

| Microbes | Growth Substrate | Conversion Rate (nmoles/min/ mg protein) |
|---|---|---|
| Obligate methylotrophs | | |
| Type I membrane structure | | |
| Methylosinus trichosporium OB3b (NRRL B-11,196) | $CH_4$ | 4.5 |
| Methylosinus trichosporium OB3b (NRRL B-11,196) | $CH_3OH$ | 2.4 |
| Type II membrane structure | | |
| Methylococcus capsulatus CRL M1 (NRRL B-11,219) | $CH_4$ | 3.2 |
| Methylococcus capsulatus CRL M1 (NRRL B-11,219) | $CH_3OH$ | 2.0 |
| Facultative methylotroph | | |
| Methylobacterium organophilium CRL 26 (NRRL B 11,222) | $CH_4$ | 1.8 |
| Methylobacterium organophilium CRL 26 (NRRL B 11,222) | $CH_3OH$ | 2.5 |
| Obligate methanol-utilizer | | |
| Pseudomonas sp. CRL 75 ATCC 21439 | $CH_3OH$ | 25.0 |
| Yeast | | |
| Hansenula polymorpha ATCC 26012 | $CH_3OH$ | 23.2 |

[a]Cells were disrupted as described and the supernatant of 10,000 × g. centrifugation was used for the enzyme assay.

TABLE XVIII

STOICHIOMETRY OF THE PRODUCTION OF 2-BUTANONE FROM 2-BUTANOL BY CELL-FREE EXTRACTS OF STAIN ATCC-21439

| Experiment | 2-Butanol Consumed (nmoles) | NAD Consumed[b] (nmole) | 2-Butanone[a] Produced (nmole) |
|---|---|---|---|
| 1 | 260 | 270 | 250 |
| 2 | 530 | 540 | 20 |

The reaction mixtures 3 ml (1.0 mg protein) were incubated at 30° C. for 10 min. (exp. 1) and for 20 min. (exp. 2) in the presence of 1.0 μmoles NAD and 10 μmoles 2-butanol.
[a]Determined gas chromatographically.
[b]Determined fluorescence spectrophotometrically. Endogenous consumption of NAD was corrected.

Purification and Properties of Secondary Alcohol Dehydrogenase

Secondary alcohol dehydrogenase (SADH) from an obligate methanol utilizer, Pseudomonas sp. ATCC 21439 was purified as follows. The cells which had been grown on methanol as the carbon source as described in the preceding examples were suspended in 300 ml. 0.05 M sodium phosphate buffer, pH 7.0 with 0.5 mM dithiothretol (buffer A) and were disrupted sonically (5×1 min.). The crude extract was separated by centrifugation. The crude extract was heat-treated at 50° C. in a water bath for 10 minutes. The resulting precipitate was removed by centrifugation. To the supernatant solution, 25 ml of protamine sulfate solution (2% solution in 0.1 M Tris base) was added dropwise with continuous stirring. After standing for 30 minutes, the extract was centrifuged. The supernatant solution was fractionated with solid ammonium sulfate. The material precipitating between 30 and 60% saturation was collected and was dialized overnight against buffer A. The The dialized material was applied to a DEAE-cellulose column (3 cm by 35 cm) that had been equilibrated with buffer A. The secondary alcohol dehydrogenase activity was eluted in the void volume. This DEAE-cellulose eluate was concentrated by ammonium sulfate fractionation.

Material precipitating between 30 and 50% ammonium sulfate saturation was collected by centrifugation and dialyzed overnight against A. This fraction was further washed and filtered through an Amicon unit with XM 50 membrane. The concentrated fraction (6 ml) inside the Amicon unit was applied to an Affi-Gel Blue column (0.8 cm×18 cm) which had been equilibrated with buffer A for affinity chromatography. The column was washed overnight with buffer A (0.18 ml./min.) and then was eluted with buffer A containing 5 mM NAD. Each 1 ml. fraction was collected. SADH activity was located in tube numbers 8–12. A summary of the purification steps is shown in Table XIX.

TABLE XIX
PURIFICATION OF SECONDARY ALCOHOL DEHYDROGENASE FROM PSEUDOMONAS SP. ATCC 21439

| Procedures | Volume (ml) | Protein (mg) | Sp. Act. (units/mg protein) | Total units | Yield (%) |
|---|---|---|---|---|---|
| Crude extract | 250 | 2698 | 25 | 67450 | 100 |
| Heat treatment | 245 | 949 | 67.5 | 64080 | 95 |
| Protamine sulfate | 260 | 526 | 103.8 | 54640 | 81 |
| $(NH_4)_2SO_4$ (30–60% sat.) | 30 | 232 | 200 | 46450 | 69 |
| DEAE-cellulose column | 150 | 42.2 | 875 | 37160 | 55 |
| Amicon filtration (XM-50) | 6 | 22.0 | 1,500 | 33050 | 49 |
| Affi-Gel Blue column | 5 | 0.34 | 65,600 | 22300 | 33 |

The purified secondary alcohol dehydrogenase enzyme (SADH) may be used directly for converting $C_3$–$C_6$ secondary alcohols to the corresponding methyl ketones by the procedures described above; however, a source of $NAD^+$ must be added to the reaction medium. One can determine the NAD-linked secondary alcohol dehydrogenase activity with a fluorescence spectrophotometer (Perkin Elmer, Model MPF 44A) by following the formation of reduced NAD (Ex 340 nm, Em 460 nm). The assay system (3 ml.) will typically contain: sodium phosphate buffer pH 7.0, 150 μmol; NAD 1.0 μmol; a given amount of enzyme preparation; and 20 μmol secondary alcohol. The reaction is started by the addition of secondary alcohol. One unit of SADH enzyme activity represents the reduction of one nmole NAD per minute.

The purification procedure outlined in Table XIX may be modified by omitting the heat-treatment. A higher specific activity can be obtained by omitting the heat-treatment (a specific activity of 45 units of SADH/mg. protein from Pseudomonas sp. ATCC 21,439 was obtained). The presence of a reducing agent such as dithrothretol in the dialyzing buffer was found essential during the dialysis of the material precipitated between 30–60% $(NH_4)_2SO_4$ saturation. In one specific experiment the Affi-Gel Blue column was scaled-up to a size of 2.5 cm×25 cm. From 10 liters of crude extract containing 200 g. protein, a 45 mg. pure SADH fraction with specific activity of 65,600 SADH units/mg. protein (33% recovery) was obtained.

Metal analysis of the purified SADH enzymes were conducted by x-ray fluorescence technique with a Phillips PW 1220C semi-automatic vacuum spectrograph. In carrying out the metal analysis the purified SADH was first washed thoroughly with deionized distilled water and then dried evenly on an Amicon XM 50 ultrafiltration membrane. This membrane was then assayed by x-ray fluorescence technique. Control experiments are taken with blank ultrafiltration membranes. The minimum amount of metal detectable qualitatively and quantitatively by this method are $>0.02$ μg. and $>0.5$ per $cm^2$, respectively. Metal analysis by this technique on the purified bacteria derived SADH enzymes showed 0.7 μg. zinc/$cm^2$ of the ultrafiltration membrane. This is equivalent to two moles of zinc per mole of SADH enzyme, or one zinc per subunit. No other metal was detected.

The molecular weight of the purified SADH was determined by acrylamide gel electrophoresis using 7.5% gel and stained with both coomassie brilliant blue and with nitro-blue tetrazolium activity stain. Sodium dodecyl sulfate-gel electrophoresis in a 10% gel system and the dissociation of enzyme protein were conducted using SDS-PAGE standards. Both the protein stain and the enzyme activity stain of the purified SADH enzymes tested showed a single protein band. The mobility on the gel electrophoresis of SADH from the distinct types of methanol-grown bacterial cells were identical. Yeast derived SADH had a faster mobility toward the anode on the gel electrophoresis. The molecular weights of several bacterial and yeast derived and purified SADH enzymes each had an identical molecular weight of 95,000 dalton as estimated by a Bio-Gel agarose A-1.5 column. SDS-gel electrophoresis of the purified enzymes showed two identical subunits of 48,000 dalton.

The optimum pH and temperatures for activity of the purified SADH was 8–9 and 30°–35° C., respectively, although wider ranges of pH and temperatures did not significantly affect the enzyme activity. The activation energy for SADH, as calculated from the Arrhenius plots of velocity vs. the reciprocal of the absolute temperature, is 19.8 K cal. The absorption spectrum of the purified SADH fraction showed no peak in the visible region.

The Michaelis constants ($K_m$) of SADH calculated from Line-Weaver-Burk plot was $1.1 \times 10^{-5}$ M for NAD. Similar reaction rates were obtained whether SADH was preincubated for 10 min. with either NAD or 2-butanol. This indicates that the addition of substrates in the SADH reaction is not an obligatory order and is rather a random mechanism. No consumption of dissolved oxygen was observed during the reaction.

The effect of metal-chelating agents and thioreagents on the activity of the purified SADH enzyme were studied. The SADH activity was inhibited as follows (% inhibition, activity measured spectrofluorometrically and each inhibitor added at a final concentration of 1 mM): iodoacetic acid, 0%; N-ethylmalemide, 6%; p-hydroxymercuribenzoate, 100%; 5,5'-dithiobis(2-nitrobenzoic acid), 100%; sodium cyanide, 0%; sodium azide, 10%; EDTA, 63%; 1,10-phenanthroline, 95%; α,α-bipyridyl, 70%; thiourea, 0%; cupric, 25%; ferric, 35%; ferrous, 50%; nickel, 20%; and $Zn^{++}$, $Co^{++}$, $Mn^{++}$, or $Mg^{++}$, 0%. Despite the fact that SADH contains 2 moles of zinc per mole of enzyme, the addition of exogenous zinc did not stimulate its activity. The possibility of ethanol or n-propanol as an inhibitor was studied. Despite their structural similarity in competing with 2-butanol for the alkyl binding site(s), both of them did not inhibit SADH activity.

The substrate specificity of purified SADH was highest for 2-propanol and 2-butanol. It also oxidized at a lower rate, 2-pentanol, 2-hexanol, acetaldehyde, propanol, cyclohexanol, butane, 1,3-diol and butane 2,3-diol.

Primary alcohols were not substrates of purified SADH. It appears that a hydrophobic carbon moiety adjacent to the secondary alcohol is required for enzyme activity.

The purified SADH enzyme was analyzed for amino acids with a Beckman Model 120B amino acid analyzer following acid hydrolysis of the enzyme. The results of the amino acid analysis are summarized in Table XX. The values are expressed as average number of residues per molecule obtained from 24, 48 and 72 hours acid hydrolysis, assuming a molecular weight of 95,000. Only two residues of cysteine were detected.

TABLE XX

AMINO ACID COMPOSITION OF PURIFIED SADH[a]

| Amino Acid | No. of Residues/ 95,000 dalton |
|---|---|
| Lysine | 52 |
| Histidine | 14 |
| Arginine | 26 |
| Cysteic Acid | 2 |
| Aspartic Acid | 78 |
| Threonine | 26 |
| Serine | 14 |
| Glutamine | 76 |
| Proline | 32 |
| Glycine | 72 |
| Alanine | 92 |
| Valine | 68 |
| Methionine | 6 |
| Isoleucine | 54 |
| Leucine | 74 |
| Tryosine | 6 |
| Phenylalanine | 28 |
| Tryptophane | 28 |

[a]The secondary alcohol dehydrogenase enzyme was purified from cells derived from Pseudomonas sp. ATCC 21,439 aerobicaly grown on methanol.

Yeast Derived SADH

As previously indicated both cell suspensions and cell-free extracts of $C_1$-compound grown yeasts enzymatically convert $C_3$–$C_6$ secondary alcohols to the corresponding methyl ketones. Further, we specifically found that cell suspensions of the yeasts: *Candida utilis* ATCC 26,387; *Hansenula polymorpha* ATCC 26,012; *Pichia* sp. NRRL Y-11,328; *Torulopsis* sp. strain $A_1$ NRRL Y-11,419; and *Kloeckera* sp. strain $A_2$ NRRL Y-11,420 grown on various $C_1$ compounds (e.g., methanol, methylamine, methylformate), ethanol and propylamine catalyzed the oxidation of $C_3$–$C_6$ secondary alcohols to the corresponding methyl ketones. Cell-free extracts of these yeasts catalyzed the NAD+-dependent oxidation of the $C_3$–$C_6$ secondary alcohols to the corresponding methyl ketones. The presence of NAD+ as an electron acceptor was essential in the case of the cell-free extract of these yeast derived enzymes. Primary alcohols were not oxidized by this purified enzyme. The molecular weight of the purified yeast derived SADH enzyme was 98,000 dalton as determined by gel filtration and the subunit size as determined by sodium dodecyl sulfate gel electrophoresis was 48,000.

It is to be noted that the molecular weight of the purified SADH whether yeast or bacteria derived is about 95,000, a determined by gel electrophoresis, but the value may vary ±3,000 due to purification procedures used and experimental error.

The activity of the purified yeast derived SADH was inhibited by sulfhydryl inhibitors and metal-binding agents. The optimum pH of the purified enzyme was determined to be about 8.

A typical yeast derived SADH enzyme was prepared as follows:

The yeasts were grown at 30° C. in 2.8 liter flasks containing 700 ml. mineral salts medium (described below) with 0.1% yeast extracts and 0.4%, v/v methanol.

| Yeast Growth Medium[a] | |
|---|---|
| $KH_2PO_4$ | 2.5 gm. |
| $NH_4NO_3$ | 2.5 gm. |
| $MgSO_4 \cdot 7H_2O$ | 0.3 gm. |
| KCl | 0.04 gm. |
| $CaCl_2$ | 0.015 gm. |
| $FeSO_4 \cdot 7H_2O$ | 1.0 mg. |
| $CuSO_4 \cdot 5H_2O$ | 0.01 mg. |
| $H_3BO_3$ | 0.02 mg. |
| $MnSO_4 \cdot 5H_2O$ | 0.04 mg. |
| $ZnSO_4$ | 0.14 mg. |
| $MoO_3$ | 0.02 mg. |
| Yeast extract | 1.0 gm. |
| Methanol | 4 ml. |

[a]The followng composition is on a per liter basis.

The cells were harvested during exponential growth by centrifugation at 12,000×g. for 15 min. The cell pellet was washed twice with 50 mM phosphate buffer, pH 7. The final pellet was resuspended in the same buffer. Cell suspensions of yeasts grown on ethanol, methylamine, and methylformate were prepared as described above using 0.4 v/v ethanol, 10 mM methylamine and 10 mM methylformate as the sole source of carbon and energy.

A 1 ml. aliquot of each washed cell suspension of yeasts grown on various carbon sources was put into 10 ml. vials at 40° C. Ten μl of secondary alcohol (2-propanol, 2-butanol, 2-pentanol and 2-hexanol) was added to the cell suspensions in an independent vial. The vials were then incubated at 30° C. on a rotary water bath shaker at 200 rpm. The product of oxidation of secondary alcohols was detected by gas chromatography retention time comparison and cochromatography with authentic standard. As shown in Table XXI the cell suspensions of yeasts catalyze the conversion of isopropanol, 2-butanol, 2-pentanol, and 2-hexanol to the corresponding methyl ketones. The products of oxidation of secondary alcohols were accumulated extracellularly and no further oxidation of products (methyl ketones) was revealed by gas chromatographic analysis.

TABLE XXI

OXIDATION OF SEC-ALCOHOLS TO KETONES BY CELL SUSPENSIONS OF YEASTS[a]

| | | Conversion Rate (μmoles/hr/mg of protein) | | | |
|---|---|---|---|---|---|
| Organism | Growth Substrate | Isopropanol to Acetone | 2-Butanol to 2-Butanone | 2-Pentanol to 2-Pentanone | 2-Hexanol to 2-Hexanone |
| *Candida utilis* | Methanol | 6.2 | 6.8 | 1.5 | 0.8 |

TABLE XXI-continued
OXIDATION OF SEC-ALCOHOLS TO KETONES BY CELL SUSPENSIONS OF YEASTS[a]

| Organism | Growth Substrate | Conversion Rate ($\mu$moles/hr/mg of protein) | | | |
|---|---|---|---|---|---|
| | | Isopropanol to Acetone | 2-Butanol to 2-Butanone | 2-Pentanol to 2-Pentanone | 2-Hexanol to 2-Hexanone |
| ATCC 26387 | Ethanol | 5.2 | 5.2 | 1.0 | 0.72 |
| | Methylamine | 5.0 | 5.0 | 1.2 | 0.61 |
| | Methylformate | 5.6 | 6.2 | 1.3 | 0.75 |
| | Propylamine | 4.2 | 4.2 | 0.9 | 0.52 |
| Hansenula polymorpha ATCC 26012 | Methanol | 5.9 | 5.8 | 1.4 | 0.72 |
| | Ethanol | 5.0 | 4.8 | 1.1 | 0.54 |
| | Methylamine | 5.2 | 4.5 | 1.2 | 0.62 |
| | Methylformate | 5.6 | 5.2 | 1.3 | 0.70 |
| | Propylamine | 4.1 | 4.0 | 0.82 | 0.48 |
| Pichia sp. NRRL-Y-11328 | Methanol | 5.2 | 6.8 | 1.2 | 0.50 |
| | Ethanol | 4.5 | 6.2 | 1.0 | 0.28 |
| | Methylamine | 4.2 | 5.1 | 0.72 | 0.31 |
| | Methylformate | 4.9 | 6.9 | 0.98 | 0.48 |
| | Propylamine | 3.2 | 2.1 | 0.60 | 0.21 |
| Torulopsis sp. Strain $A_1$ (NRRLY-11,419) | Methanol | 4.5 | 4.9 | 1.0 | 0.21 |
| | Ethanol | 4.2 | 4.7 | 1.2 | 0.20 |
| | Methylamine | 4.3 | 4.5 | 0.9 | 0.12 |
| | Methylformate | 4.5 | 4.9 | 1.1 | 0.25 |
| | Propylamine | 3.2 | 3.8 | 0.62 | 0.10 |
| Kloeckera sp. Strain $A_2$ (NRRLY-11,420) | Methanol | 4.8 | 5.9 | 1.2 | 0.25 |
| | Ethanol | 4.5 | 5.7 | 1.0 | 0.12 |
| | Methylamine | 4.0 | 5.4 | 1.0 | 0.10 |
| | Methylformate | 4.9 | 5.9 | 1.2 | 0.28 |
| | Propylamine | 4.0 | 4.2 | 0.92 | 0.11 |

[a]The products of oxidation were identified by gas chromatography retention time comparison and co-chromatography with authentic standard. Analysis also revealed that no further oxidation of products (methylketones) occurred.

Cell suspensions (2 g. wet weight) of packed cells in 10 ml. of 50 mM sodium phosphate buffer, pH 7.0 at 4° C. were disrupted by sonication with a Megason ultrasonic disintegration. The sonicated cell suspensions were centrifuged for 15 minutes at 30,000×g. The supernatant liquid was termed the crude extracts.

Purification of Secondary Alcohol Dehydrogenase Derived from Yeast

Large scale cultures of Pichia sp. NRRL Y-11,328 were grown with aeration at 30° C. in a 14-liter New Brunswick f fermentor in a mineral salt medium containing methanol (0.4%, v/v) as the sole carbon source. The cells (200 g., wet weight) were suspended in 50 mm sodium phosphate buffer, pH 7.0, containing 1 mM dithiothreitol (buffer A), and crude extracts were prepared as described previously. To the crude extracts, 18 ml. of protamine sulfate solution [2% solution in 0.1 M tris (hydroxymethyl) aminomethane (tris) base] was added dropwise with continuous stirring. After standing for 30 min., the extracts were centrifuged at 20,000×g. for 60 min. The supernatant solution was fractionated with solid ammonium sulfate. Extracts were brought to 50% of saturation with respect to ammonium sulfate by addition of 313 g. of the salt per liter of extract. Precipitated proteins was removed by centrifugation, and 137 g. of ammonium sulfate was added per liter of the supernatant liquid to bring it to 70% of saturation. Material precipitating between 50 and 70% of saturation was collected by centrifugation and dissolved in buffer A. This preparation was dialyzed overnight against buffer A, and the dialyzed material was applied to a DEAE-cellulose column (5×40 cm) that had been equilibrated with buffer A. The sample was washed with 200 ml. of buffer A and eluted with 2 liters of buffer A that contained NaCl in a linear gradient running from a concentration of 0 to 0.5 M. Fractions of 15 ml. were collected. Fractions containing secondary alcohol dehydrogenase activity were pooled and were termed DEAE-cellulose eluate. The DEAE-cellulose eluate was concentrated by ammonium sulfate fractionation. Material precipitating between 50 and 70% of ammonium sulfate saturation was collected by centrifugation and dissolved in buffer A. This preparation was dialyzed overnight against buffer A, and 4 ml. samples were passed through a Bio-Gel agarose A-1.5 column (2.5×100 cm) that had been equilibrated with buffer A. Fractions containing constant specific activity of enzyme were pooled and concentrated by Amicon ultrafiltration using an XM 50 filter.

The reaction mixture, in a total of 3.0 ml., contained 50 mM phosphate buffer, pH 7.0, 20$\mu$ mole NAD+, cell extracts (1 ml.). The reactions were started by the addition of 50 moles of secondary alcohol (isopropanol, 2-butanol, 2-pentanol, 2-hexanol) and the rate of production of methyl ketones (acetone, 2-butanone, 2-pentanone, 2-hexanone) was measured by gas chromatography.

The ketone product obtained from oxidation of secalcohols by cell extracts of organisms were estimated by flame ionization gas chromatography by using a stainless steel column (12 ft. by ⅛ in.) packed with 10% Carbowax 20 M on 80/100 chromosorb w column (Perkin Elmer Corp., Norwalk, Conn.). The column temperature was maintained isothermally at 130° C. and the carrier gas flow was 30 ml. of helium per min. The various ketone products (acetone, 2-butanone, 2-pentanone, 2-hexanone) were identified by retention time comparisons and co-chromatography with authentic standard. The protein content of cell-suspensions was determined by the Lowry et al. method.

Secondary alcohol dehydrogenase activity was measured spectrophotometrically at 340 nm with a NAD+ as an electron acceptor. The reaction mixture, in a total 3.0 ml., contained 50 mM phosphate buffer, pH 8.0, 5μ moles NAD+, crude extracts, and subtrate. The reactions were started by addition of 100 μl of 0.1 M substrate and the rate of NAD+ reduction was measured. Protein concentration was determined by the method of Lowry et al.

Cell free extracts derived from yeasts, *Candida utilis* ATCC 26,387, *Hansenula polymorpha* ATCC 26,012, *Pichia* sp. NRRL Y-11,328, *Torulopsis* sp. strain $A_1$ NRRL Y-11,419 and *Kloeckera* sp. strain $A_2$ NRRL Y-11,420 grown on methanol catalyzed an NAD+-dependent oxidation of secondary alcohols (isopropanol, 2-butanol, 2-pentanol, 2-hexanol) to the corresponding methyl ketones (acetone, 2-butanone, 2-pentanone, 2-hexanone). The rate of production of methyl ketones from secondary alcohols are shown in Table XXII. Oxidation of secondary alcohols were also estimated spectrophotometrically by measuring the reduction of NAD+. The specific activities (nmoles NAD+ reduced per min. per mg. protein) of 78, 85, 105, 62, and 90 were obtained with extracts derived from *Candida utilis* ATCC 26,387, *Hansenula polymorpha* ATCC 26,012, *Pichia* sp. NRRL Y-11,328 *Torulopsis* sp. NRRL Y-11,419 strain $A_1$ and *Kloeckera* sp. strain $A_2$ NRRL Y-11,420, respectively, using 2-butanol as a substrate.

TABLE XXII
OXIDATION OF SECONDARY ALCOHOLS TO METHYLKETONE BY CELL EXTRACTS OF YEASTS

| Organisms | Conversion Rate[a] μmoles/hr/mg Protein | | | |
|---|---|---|---|---|
| | Isopropanol to Acetone | 2-Butanol to 2-Butanone | 2-Pentanol to 2-Pentanone | 2-Hexanol to 2-Hexanone |
| *Candida utilis* ATCC 26,387 | 4.5 | 4.92 | 0.82 | 0.45 |
| *Hansenula polymorpha* ATCC 26,012 | 4.8 | 5.2 | 1.0 | 0.51 |
| *Pichia* sp. NRRL-Y-11,328 | 5.5 | 6.2 | 1.2 | 0.60 |
| *Torulopsis* sp. strain $A_1$ NRRL-Y-11,419 | 4.5 | 4.9 | 1.0 | 0.21 |
| *Kloeckera* sp. strain $A_2$ NRRL-Y-11,420 | 4.8 | 5.9 | 1.2 | 0.25 |

[a]Reactions were carried out as described above. The products of oxidation of secondary alcohols were identified and estimated by gas chromatography.

The SADH enzyme was eluted from a DEAE-cellulose column at 0.08 M NaCl concentration. The overall 60-fold purification was achieved from crude extracts. Purity of the enzyme preparation was examined by polyacrylamide gel electrophoresis. The purified enzyme preparations migrated as a single protein band when subjected to electrophoresis on polyacrylamide gel. Table XXIII illustrates a summary of the purification steps and an analysis of the products at the end of each step.

The substrate specificity of the purified secondary alcohol dehydrogenase was examined spectrophotometrically. Among various secondary alcohls tested, the enzyme catalyzed the oxidation of isopropanol, 2-butanol, 2-pentanol, and 2-hexanol.

2-Heptanol, 2-octanol, methanol, ethanol, propan-1-ol, butan-1-ol, pentan-1-ol, 1,2-propandiol, 1,2-butandiol and 1,3-butandiol were not oxidized by the purified enzyme.

The purified enzyme required NAD+ as an electron acceptor. NADP, phenazine methosulfate, potassium ferricyanide, cytochrome c, 2,6-dichlorophenol indophenol, flavin adenine dinucleotide could not act as electron carrier.

Various primary alcohols not oxidized by secondary alcohol dehydrogenase were tested as potential inhibitors of enzyme activity. Enzyme activity was not inhibited by primary alcohols when tested at $10^{-3}$ M. Among various sulfhydryl inhibitors and metal-binding compounds tested, p-hydroxy mercaribenzoate, glutathione, imidazole and 1,10 phenanthroline were strongly inhibited secondary alcohol dehydrogenase activity. Enzyme activity was also inhibited by heavy metals such as silver nitrate, mercuric thiocyanate and cupric sulfate.

TABLE XXIII
PURIFICATION OF SECONDARY ALCOHOL DEHYDROGENASE FROM *Pichia* sp. NRRL Y-11,328[a]

| Step | Vol. (ml) | Protein (mg) | Units | Sp. activity (Units/mg. of Protein) | Yield % |
|---|---|---|---|---|---|
| Crude extracts | 875 | 21,875 | 2391375 | 109 | 100 |
| 2. Protamine sulfate treatment | 890 | 21,360 | 2370960 | 111 | 99 |
| 3. Ammonium sulfate fractionation (50-70% saturation) | 117 | 3,090 | 1820010 | 589 | 76 |
| 4. DEAE-cellulose eluate | 55 | 200 | 706800 | 3534 | 29 |
| 5. Bio-Gel chromatography | 19 | 52 | 312624 | 6012 | 13 |

[a]Secondary alcohol dehydrogenase activity was estimated spectrophotometrically as described above using 2-butanol as a substrate. Specific activity was expressed as nanomoles of NAD+ reduced per min per mg of protein.

Acetone and 2-butanone was detected as the product of oxidation of isopropanol and 2-butanol, respectively, by the purified enzyme. The amount of NAD+ reuced and product formed is consistent with quantitative oxidation of both substrates. These results are shown in Table XXIV.

TABLE XXIV
STOICHIOMETRY OF ISOPROPANOL AND SEC-BUTANOL OXIDATION BY THE PURIFIED SECONDARY ALCOHOL DEHYDROGENASE

| Substrate (μmoles) | | NAD+ Reduced[a] (μmoles) | Product formed[b] (μmoles) | |
|---|---|---|---|---|
| Isopropanol | 5.7 | 5.4 | Acetone | 5.5 |
| 2-Butanol | 6.0 | 5.9 | 2-Butanone | 5.7 |

[a] The estimation of NAD+ reduced was measured spectrophotometrically at 340 nm.
[b] The estimation of products was detected by gas chromatography as described in the methods.

ALKANE OXIDATION SYSTEM

Both cell suspensions (particulate fraction) and cell-free particulate fraction of methane-grown methylotroph microorganisms are capable of catalyzing the conversion of $C_3$–$C_6$ n-alkanes to the corresponding alcohols including secondary alcohols. The conditions for preparing the cell suspensions or the cell-free particulate fractions from methane-grown methylotroph microorganisms is the same as described above. The cell-free particulate fraction requires the presence of oxygen and NADH as an electron donor. The conversion to the alcohol was inhibited by metal-binding agents which suggests the involvement of metal ion(s) in the conversion of the alkanes to secondary alcohols. Propylene was also found to inhibit the conversion which suggests that the propylene and n-alkane (e.g., propane) are competing for the same enzyme system(s). Ascorbate and reduced nicotinamide adenine dinucleotide phosphate (NADPH) could also be utilized as an electron donor in place of NADH for the conversion. Tables XXV and XXVI show the conversion of $C_3$–$C_6$ n-alkanes to the corresponding secondary alcohols using cell suspensions and cell-free particulate fractions, respectively, of methane-grown methylotroph microorganisms.

TABLE XXV
CONVERSION OF N-ALKANES TO SECONDARY ALCOHOLS BY MICROORGANISMS[a]

| | | Conversion Rate μmoles/hr/[5]mg. protein | | | |
|---|---|---|---|---|---|
| Microorganisms | Growth Substrate | n-propane to 2-propanol | n-butane to 2-butanol | n-pentane to 2-pentanol | n-hexane to 2-hexanol |
| *Methylosinus trichosporium* (OB3b, NRRL-B-11,196) | Methane | 2.5 | 1.5 | 0.06 | 0.01 |
| *Methylococcus capsulatus* (Texas, ATCC 19,069) | Methane | 1.1 | 1.0 | 0.032 | 0.01 |
| *Methylobacter capsulatus* (Y, NRRL-B-11,201) | Methane | 0.20 | 0.09 | — | — |
| *Methylosinus sp.* (CRL-15, NRRL-B-11,202) | Methane | 2.1 | 1.2 | — | — |
| *Methylobacterium sp.* (CRL-26, NRRL-B-11,208) | Methane | 1.4 | 0.80 | 0.01 | 0.007 |
| *Methylomonas sp.* (CRL-17, NRRL-B-11,208) | Methane | 1.6 | 1.2 | — | — |

[a] The product secondary alcohols were identified and estimated by GC retention time comparison and co-chromatography with authentic standards.

TABLE XXVI
HYDROXYLATION OF N-ALKANES TO SECONDARY ALCOHOLS BY PARTICULATE P(40)[a] FRACTION OF METHYLOTROPHS:

| | Conversion Rate μmoles/hr/2.0mg. of protein | |
|---|---|---|
| Organisms | n-propane to 2-propanol | n-butane to 2-butanol |
| *Methylosinus sp.* (CRL-15, NRRL-B-11,202) | 1.5 | 0.89 |
| *Methylococcus capsulatus* (Texas, ATCC 19,069) | 1.2 | 0.92 |
| *Methylosinus trichosporium* (OB3b, NRRL-B-11,196) | 1.32 | 0.79 |
| *Methylobacterium sp.* (CRL-26, NRRL-B-11,222) | 1.0 | 0.61 |

[a] Particulate P(40) fraction was prepared as follows: Cell-suspensions at 4° C. were disintegrated through a French Pressure cell and centrifuged at 4000 × g. for 15 min. to remove unbroken bacteria. The supernatant solution was then centrifuged at 40,000 × g. for 30 min. at 4° C., yielding the particulate P(40) and soluble S(40) fractions. The products were identified by gas chromatography and co-chromatography with authentic standard.

Table XXVII shows that cell suspensions of methane-grown methylotroph microorganisms convert $C_1$–$C_2$ alkanes to the corresponding alcohols and propane and butane are converted to a plurality of oxidation products, including primary and secondary alcohols, methyl ketones and aldehydes.

TABLE XXVII
CONVERSION OF n-ALKANES TO OXIDATION PRODUCTS[a]

| | | Conversion Rate μmoles/hr./mg./protein | |
|---|---|---|---|
| Substrate | Products | *Methylosinus trichosporium* OB3b NRRL B-11,196 | *Methylococcus capsulatus* CRL M1 NRRL B-11,219 |
| Methane | Methanol | 1.5 | 2.5 |
| Ethane | Ethanol | 1.3 | 2.0 |
| Propane | 1-Propanol | 0.4 | 0.5 |
| Propane | 2-Propanol | 0.6 | 0.7 |
| Propane | Propanol | 0.1 | 0.2 |
| Propane | Acetone | 0.2 | 0.3 |
| Butane | 1-Butanol | 0.3 | 0.4 |
| Butane | 2-Butanol | 0.4 | 0.5 |
| Butane | 2-Butanone | 0.1 | 0.2 |
| Butane | n-butanol | 0.1 | 0.2 |

[a] Cell-suspensions of methane-grown methylotroph microorganisms indicated in 0.15 M phosphate buffer, pH 7.0 incubated in the alkanes as indicated at 3° C. The oxidation products were determined by g.l.c.

Leadbetter and Foster (*Archiv. fur Mikrobiologie,* 35:92–104 (1960)) reported that methane grown *Pseudomonas methanica co-oxidized propane and butane to their corresponding methyl ketones. They stated that resting cell-suspensions of methane-grown cells, however, did not oxidize propane or butane. Later, Lukins and Foster (J. Bacteriol.,* 85:1074–1086 (1963)) reported that propane-grown *Mycobacterium smegmatis* 422 oxidized n-alkanes to their corresponding methyl ketones. We have found and demonstrated that resting cell-suspensions of methane-grown cells oxidize $C_3$–$C_6$ alkanes to their corresponding secondary alcohols and methyl ketones in the absence of growth substrates. In addition, we have demonstrated for the first time the conversion of $C_3$–$C_6$ secondary alcohols to their corresponding methyl ketones by resting cell suspensions (particulate fraction) of either alkane-grown or alcohol grown cells. Succinate-grown cells do not have SADH activity, suggesting that either alkane or alcohol is required for inducing the enzyme.

As shown above, cell suspensions of these new cultures as well as known $C_1$-utilizers grown on either methane or methanol oxidized secondary alcohols to their corresponding methyl ketones. The cultures tested were selected from distinct general and they were compared for their optimal conditions in the production of 2-butanone. These cultures were: *Methylosinus trichosporium* OB3b (NRRL B-11,196) (a Type I obligate methane-utilizer); Methylobacterium organophilum CRL 26 (NRRL B-11,222) (a facultative methane-utilizer); *Hansenula polymorpha* ATCC 26012; and Pseudomonas sp. ATCC 21439 (an obligate methanol-utilizer). The rate of 2-butanone production was linear for the first 4 hours of incubation for all five cultures tested. The yeast culture had the highest production rate. The optimum temperature for the production of 2-butanone was 35° C. for all the bacteria tested. The yeast culture had a higher temperature optimum (40° C.), and a reasonably high 2-butanone production rate was also observed at 45° C. for this yeast. The production of 2-butanone was affected by substrate concentration and cell concentration. The inhibition by metal-chelating agents of the production of 2-butanone suggests the involvement of metal(s). No product (2-butanone) inhibition was observed in any of the cell-suspensions from all the five cultures tested.

We have found that cell-free soluble extracts from sonically disrupted cells also oxidize 2-butanol to 2-butanone. The cell-free system requires addition of a cofactor, specifically NAD, for its activity. One of the explanations for the rate decreases in 2-butanone production after 4 hours of incubation, therefore, may be the depletion of NAD in the cell suspensions.

Nicotinamide adenine dinucleotide (NAD) was found to be a requirement for the oxidation of $C_3$–$C_6$ secondary alcohols in the cell-free SADH system. Other cofactors tested (including PMS, GSH, FAD, potassium ferricyanide, dichlorophenol indophenol, and NADP) were not effective.

The molecular weight of the pure SADH as estimated by a Bio-Gel agarose A-1.5 column is 95,000 dalton. Acrylamide gel electrophoresis of the purified SADH fraction from the affinity chromatography showed a single protein band. The Km values for 2-butanol and NAD are 0.25 mM and 0.011 mM, respectively. The pH optimum for SADH activity was around 8–9 (0.05 M sodium phosphate buffer for pH 5 to 8; 0.05 M sodium pyrophosphate buffer for pH 8 to 11).

SADH oxidizes $C_3$–$C_6$ secondary alcohols with the following relative percent rate: 2-propanol (85%), 2-butanol (100%), 2-pentanol (5%), 2-hexanol (2%), acetaldehyde (4%), propanol (2%), cyclohexanol (4%), butane 1,3-diol (2%), and butane 2,3-diol (2.5%). The following compounds tested were not oxidized by SADH: 2-heptanol to 2-decanol, formaldehyde, butanal to decanal, benzaldehyde, methanol to n-decanol, isobutanol, phenol, butane 1,2-diol, and succinic acid. It seems that a hydrophobic carbon moiety adjacent to the secondary alcohol is required for the enzyme activity.

The SADH activity was inhibited by metal-chelating agents in the following order (percent inhibition): 1,10-phenanthroline (95%), α,α-bipyridyl (70%), EDTA (63%), and sodium azide (10%). This suggests possible metal involvement. However, the activity was not inhibited by sodium cyanide or thiourea. The enzyme activity was also inhibited by strong thio inhibitors such as p-hydroxy mercuribenzoate (100%) and 5,5′-dithiobis (2-nitrobenzoic acid) and was not inhibited by less potent thio inhibitors such as iodoacetic acid or N-ethylmaleimide. The physiological significance of this SADH in methylotrophs as well as other gaseous hydrocarbon utilizers is not known. However, possessing this enzyme is of great advantage to the organism as its growth yield, when growing on gaseous alkanes as the sole source of carbon and energy, could be exclusively NAD(P)H-dependent. Secondary alcohols are intermediates in the oxidation of n-alkanes by either Pseudomonas or Mycobacterium. The methane monooxygenase from *Methylococcus capsulatus* (Bath) also oxidizes n-alkanes to both primary and secondary alcohols. The fact that SADH is also present in the methanol-grown cells indicates that the enzyme is not induced by n-alkanes.

The metabolism of the obligate methylotrophs is uniquely dependent on a one-carbon compound (formaldehyde) for the biosynthesis of certain essential cellular constituents. This compound can be obtained from methane and methanol, but is unobtainable from the non-growth-supporting compounds.

NAD-dependent alcohol dehydrogenase and PMS-dependent methanol dehydrogenase are well characterized enzymes. Both of these dehydrogenases have a broad specificity toward primary alcohols. Recently, Metha (*J. Bacteriol.,* 124:1165–1167 (1975)) reported an NAD-linked alcohol dehydrogenase from a yeast grown on methanol. This primary alcohol dehydrogenase also oxidizes 2-propanol. In addition, the report stated that this alcohol dehydrogenase was very unstable that it lost all of its enzyme activity within 24 hours after fourfold purification. Results from our preliminary studies, however, indicate that our secondary alcohol dehydrogenase is a secondary alcohol-specific enzyme with highest activity on 2-propanol and 2-butanol, and has no activity towards primary alcohols.

What is claimed is:

1. A process for converting a $C_3$–$C_6$ secondary alcohol to the corresponding methyl ketone comprising oxidizing said alcohol by contacting said alcohol in a medium, under aerobic conditions, with microbial cells derived from a methylotrophic microorganism or an enzyme preparation derived from said cells, wherein said microorganism has been previously grown under aerobic conditions in a nutrient medium containing a carbon-containing compound which provides the carbon and energy source for growth of the cells and induces $C_3$–$C_6$ secondary alcohol dehydrogenase enzyme activity in said cells, and wherein said microorganism is selected from the group consisting of:

| | | |
|---|---|---|
| *Methylosinus trichosporium* | (CRL 15 PM1) | NRRL B-11,202; |
| *Methylosinus sporium* | (CRL 16 PM2) | NRRL B-11,203; |
| *Methylocystis parvus* | (CRL 18 PM4) | NRRL B-11,204; |
| *Methylomonas methanica* | (CRL M4P) | NRRL B-11,205; |
| *Methylomonas methanica* | (CRL 21 PM7) | NRRL B-11,206; |
| *Methylomonas albus* | (CRL M8Y) | NRRL B-11,207; |
| *Methylomonas streptobacterium* | (CRL 17 PM3) | NRRL B-11,208; |
| *Methylomonas agile* | (CRL 22 PM9) | NRRL B-11,209; |
| *Methylomonas rubrum* | (CRL M6P) | NRRL B-11,210; |
| *Methylomonas rubrum* | (CRL 20 PM6) | NRRL B-11,211; |
| *Methylomonas rosaceus* | (CRL M10P) | NRRL B-11,212; |
| *Methylomonas rosaceus* | (CRL M7P) | NRRL B-11,213; |
| *Methylobacter chroococcum* | (CRL M6) | NRRL B-11,214; |
| *Methylobacter chroococcum* | (CRL 23 PM8) | NRRL B-11,215; |
| *Methylobacter bovis* | (CRL M1Y) | NRRL B-11,216; |
| *Methylobacter bovis* | (CRL 19 PM5) | NRRL B-11,217; |
| *Methylobacter vinelandii* | (CRL M5Y) | NRRL B-11,218; |
| *Methylococcus capsulatus* | (CRL M1) | NRRL B-11,219; |
| *Methylococcus minimus* | (CRL 24 PM12) | NRRL B-11,220; |
| *Methylococcus capsulatus* | (CRL 25 PM13) | NRRL B-11,221; |
| *Methylobacterium organophilum* | (CRL 26 R6) | NRRL B-11,222; |
| Pichia sp. | (CRL-72) | NRRL-Y-11,328; |
| Torulopsis sp. | ($A_1$) | NRRL-Y-11,419; |
| Kloeckera sp. | ($A_2$) | NRRL-Y-11,420; | and mutants thereof wherein said methyl ketone is produced in isolable amounts.

2. The process of claim 1 wherein the enzyme preparation is a bacterial or yeast cell suspension which has been grown on a methyl radical donating compound.

3. The process of claim 2 wherein said enzyme preparation comprises microbial cells.

4. The process of claim 1 wherein said enzyme preparation is cell-free and the medium additionally contains nicotinamide adenine dinucleotide.

5. The process of claim 4 wherein the enzyme preparation is a bacterial- or yeast-derived cell-free extract.

6. The process of claim 4 wherein the enzyme preparation is substantially purified $C_3$–$C_6$ secondary alcohol dehydrogenase.

7. The process of claim 4 wherein the conversion is carried out at a temperature ranging from about 5° to about 55° C. and at a pH in the range from about 4 to about 9.

8. The process of claim 4 wherein the enzyme is immobilized.

9. The process of claim 4 wherein the conversion is carried out batchwise.

10. The process of claim 4 wherein the conversion is carried out in a continuous manner and said enzyme is immobilized.

11. The process of claim 4 wherein the enzyme, $C_3$–$C_6$ secondary alcohol dehydrogenase, has a molecular weight of 95,000±3,000 dalton as determined by Bio-gel column chromatography and two zinc atoms per molecule of protein.

* * * * *